(12) United States Patent  
Sykes (10) Patent No.: US 7,498,023 B2  
(45) Date of Patent: Mar. 3, 2009

(54) BLOCKADE OF T CELL MIGRATION INTO EPITHELIAL GVHD TARGET TISSUES AS AN APPROACH TO ACHIEVING ANTI-TUMOR EFFECTS AGAINST LYMPHOHEMATOPOIETIC MALIGNANCIES WITHOUT GVHD

(75) Inventor: Megan Sykes, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 549 days.

(21) Appl. No.: 10/437,707

(22) Filed: May 14, 2003

(65) Prior Publication Data

US 2004/0067220 A1 Apr. 8, 2004

Related U.S. Application Data

(63) Continuation of application No. PCT/US01/43797, filed on Nov. 14, 2001.

(60) Provisional application No. 60/248,332, filed on Nov. 14, 2000.

(51) Int. Cl.
*A01N 63/00* (2006.01)
*C12N 5/08* (2006.01)
*A61K 35/26* (2006.01)

(52) U.S. Cl. .................. 424/93.1; 424/577; 435/372

(58) Field of Classification Search ............... None
See application file for complete search history.

(56) References Cited

U.S. PATENT DOCUMENTS 6,558,662 B2 * 5/2003 Sykes et al. ............... 424/93.1

FOREIGN PATENT DOCUMENTS

WO WO 95/24913 9/1995
WO WO 00/11950 * 3/2000
WO WO 01/95928 A2 12/2001

OTHER PUBLICATIONS

Feldman et al., Transplant. Proc. 1998, 30, 4126-4127.*
Mestas et al., J. of Immunology, 2004, 172, pp. 2731-238.*

Murai et al., J of Clinical Investigation, 1999, V. 104, pp. 49-57.*
Murai et al., "Active Participation of CCR5+CD8+ T Lymphocytes in the Pathogenesis of Liver Injury in Graft-Versus-Host Disease," Journal of Clinical Investigation, vol. 104, No. 1, Jul. 1999, pp. 49-57.
Howell et al., "Role of Intercellular Adhesion Molecule-1 and Lymphocyte Function-Associated Antigen-1 During Nonsuppurative Destructive Cholangitis in a Mouse Graft-Versus-Host Disease Model," Hepatology, vol. 29, No. 3, Mar. 1999, pp. 766-776.
Schlegel et al., "Inhibition of T Cell Costimulation by VCAM-1 Prevents Murine Graft-Versus-Host Disease Across Minor Histocompatibility Barriers," Journal of Immunology, vol. 155, No. 8, 1995, pp. 3856-3865.
Hancock et al., "Chemokines and Their Receptors in Allograft Rejection," Current Opinion in Immunology, vol. 12, No. 5, Oct. 2000, pp. 511-516.
Slavin et al., "Nonmyeloablative Stem Cell Transplantation and Cell Therapy as an Alternative to Conventional Bone Marrow Transplantation with Letal Cytoreduction for the Treatment of Malignant and Nonmalignant Hematologic Diseases," Blood, vol. 91, No. 3, Feb. 1998, pp. 756-763.
Abstract #3334 XP-001068660, Mapara et al., "Expression of Chemokines in GVHD Target Organs Following Lethal Irradiation and Syngeneic or Allogeneic Bone Marrow Transplantation".
Kawai et al., "Mixed Allogeneic Chimerism and Renal Allograft Tolerance in Cynomolgus Monkeys," Transplantation, vol. 59, No. 2, Jan. 1995, pp. 256-262.
Storb et al., "Stable Mixed Hematopoietic Chimerism in DLA-Identical Littermate Dogs Given Sublethal Total Body Irradiation Before and Pharmacological Immunosuppression After Marrow Transplantation," Blood, vol. 89, No. 8, 1997, pp. 3048-3054.
Abstract #1856 XP-002101606, Spitzer et al., "Clinical Remission of Refractory non-Hodgkin's Lymphoma Induced by Allogeneic Bone Marrow Transplantation (BMT) with Mixed Chimerism in Non-Myeloablated Recipents".
Sykes et al., "Induction of High Levels of Allogeneic Hematopoietic Reconstitution and Donor-Specific Tolerance Without Myelosuppressive Conditioning," Nature Medicine, vol. 3, No. 7, Jul. 1997, pp. 783-787.

* cited by examiner

*Primary Examiner*—Michail A Belyavskyi
(74) *Attorney, Agent, or Firm*—Margo H. Fuman; Choate, Hall & Stewart LLP (57) ABSTRACT

Antagonists of T cell migration are used to reduce GVHD in recipients of hematopoietic cell grafts. The administration of antagonists of T cell migration can be used in combination with conventional methods of bone marrow transplantation and in combination with the administration of donor leukocytes.

16 Claims, 3 Drawing Sheets

BLOCKADE OF T CELL MIGRATION INTO EPITHELIAL GVHD TARGET TISSUES AS AN APPROACH TO ACHIEVING ANTI-TUMOR EFFECTS AGAINST LYMPHOHEMATOPOIETIC MALIGNANCIES WITHOUT GVHD

CROSS REFERENCE TO RELATED APPLICATIONS

This application is a continuation of PCT/US01/43797, filed Nov. 14, 2001, which claims the benefit under 35 U.S.C. § 119(e) of U.S. Provisional Appl. No. 60/248,332, filed Nov. 14, 2000.

STATEMENT REGARDING FEDERALLY SPONSORED RESEARCH OR DEVELOPMENT

The work herein was supported by a grant from the National Institutes of Health. The government may have certain rights in the invention.

BACKGROUND OF THE INVENTION

The invention relates to the treatment of hematologic disorders, e.g., disorders characterized by unwanted cells of hematopoietic origin, e.g., hematologic cancers.

Bone marrow transplantation (BMT) has yet to realize its full potential for the treatment of hematologic malignancies. The major obstacle to further advancement is graft-versus-host disease (GVHD), which is best be prevented by removing T cells from the donor marrow. Unfortunately, T cell-depletion has been associated with increased rates of engraftment failure (Martin, et al., *Bone Marrow Transplant,* 3:445-456 (1988)) and leukemic relapse (Butturini, et al., *Bone Marrow Transplant,* 3:265-279 (1988)). Despite improvements in pharmacologic GVHD prophylaxis, severe acute and chronic GVHD are still major complications of HLA-matched sibling bone marrow transplantation (Storb, et al., *Blood,* 73:1729-1734 (1989)) and (Sullivan, et al., *Bone Marrow Transplantation: Current Controversies,* 511 (1989)). Immunosuppressive drugs used for GVHD prophylaxis also increase the relapse rate for certain types of leukemia (Storb, et al., *Blood,* 73:1729-1734 (1989)); (Atkinson, et al., *Aust. N. Z. J. Med.,* 4:587-593 (1989)); (Sullivan, et al., *Blood,* 73:1720-1728 (1989)); (Barrett, et al., *Blood,* 74:862-871 (1989)); and (Denham, et al., *Br. J. Cancer,* 47:791-795 (1983)). The subjects receiving allogeneic BMT are, nevertheless, a fortunate select group: most subjects do not have an HLA-matched sibling or a phenotypically-matched unrelated donor, and therefore do not have the option of BMT. Attempts to perform BMT between extensively HLA-mismatched donor-recipient pairs have been associated with a prohibitively high incidence of severe GVHD (Clift, et al., *Ann. Rev. Immunol.,* 5:43-64 (1987)) and of failure of engraftment, a potentially lethal complication in myeloablated recipients (Anasetti, et al., *New Engl. J. Med.,* 320:197-204 (1989)); (O'Reilly, et al., *Transplantation. Proc.,* 17:455 (1985)); and (Fleischhauer, et al., *New Engl. J. Med.,* 323:1818-1822 (1990)). Studies in animal models, however, have shown that MHC-disparate bone marrow transplants mediate anti-leukemic and anti-lymphoma effects that greatly exceed those achieved with MHC-matched BMT (Aizawa, et al., *Transplantation,* 52:885-889 (1991)); (Sykes, et al., *Transplant. Proc.,* 21:3022-3024 (1989)). Clinical data also support the presence of increased graft-versus-leukemia/lymphoma (GVL) effects in the setting of HLA-mismatched BMT (Beatty, et al., *Blood,* 81:249-253 (1993)); (Drobyski, et al., *Blood,* 84:1980-1987 (1994)); (Sierra, et al., *Blood,* 89:4226-4235 (1997)), but this advantage has unfortunately been offset by a higher incidence of severe GVHD. Animal and clinical evidence for increased GVL effects occurring with the use of MHC-mismatched donors probably reflects the fact that the frequency of T cells in the unprimed repertoire that recognizes allogeneic MHC molecules is orders of magnitude greater than that recognizing any single non-MHC (minor or tumor-specific) antigen or multiple minor histoincompatibilities. Therefore, if the morbidity associated with GVHD and engraftment failure is avoided, the ability to perform HLA-mismatched BMT might be associated with GVL effects of sufficient magnitude to eradicate the most refractory hematologic malignancies. For example, subjects with chemo- and radio-resistant non-Hodgkins lymphomas (NHL) currently have few therapeutic options other than palliation. Results of closely-HLA-matched related allogeneic BMT have been disappointing, with durable remissions attained in 0-23% of subjects. Consequently, subjects with refractory NHL are not usually considered to be candidates for allogeneic BMT.

Many hematologic malignancies, such as chronic lymphocytic leukemia (CLL) and multiple myeloma, predominantly afflict older persons, in whom the increased risk of GVHD and other transplant-related complications rule out BMT as a therapeutic option. CLL is considered to be an incurable and ultimately fatal disease. Although promising results were achieved in a recent trial of allogeneic BMT in younger subjects with CLL (Rabinowe, et al., *Blood,* 82:1366-1376 (1993)), BMT has not been widely used for this leukemia, despite the fact that there are no known curative therapies to offer this group of subjects. Therefore, there is a continuing need to reduce the risk of GVHD in BMT immunocompetent subjects and to develop curative therapies for adult, immunocompetent subjects suffering from hematologic or lymphohematologic disorders, such as refractory, aggressive NHL.

SUMMARY OF THE INVENTION

The invention relates to methods of reducing GVHD in recipients of hematopoietic cell grafts. More particularly, the invention relates to the administration of an antagonist of T-cell migration to reduce GVHD associated with T-cell migration into the tissues of hematopoietic cell graft recipients. Thus, the invention provides improved methods for transplanting hematopoietic cells into a recipient.

In a first aspect, the invention provides methods for reducing GVHD in a recipient of a hematopoietic cell graft by administering at least one antagonist of T-cell migration. The recipient of the hematopoietic cell graft may have a hematologic malignancy or a non-neoplastic hematologic disorder.

In a second aspect, the invention provides methods for reducing GVHD in a recipient of donor hematopoietic stem cells and donor leukocytes by administering at least one antagonist of T-cell migration. Optionally, the recipient of the donor hematpoietic stem cells and donor leukocytes has a hematologic malignancy.

Preferred antagonists of T-cell migration include antagonists of chemokines and antagonists of adhesion molecules. The methods of the invention may further include the administration of myeloablative or myeloreductive non-myeloablative treatments to the recipient of the cell graft. The administration of myeloablative or myeloreductive non-myeloablative treatments may be used to induce mixed hematopoietic chimerism or full hematopoietic chimerism. The methods of the invention may also further include the administration of immunosuppresive treatments. Thymic space creating treatments may also be used in combination with the methods of the invention.

DETAILED DESCRIPTION OF THE INVENTION

The inventor has discovered that GVHD associated with hematopoietic cell grafts can be reduced by blocking molecules that allow donor-T cells to migrate into host tissues, thereby causing GVHD. Studies in the murine models have demonstrated clearly that the presence of a graft-versus-host (GVH) alloreaction is in itself insufficient to induce GVHD. GVH alloresponses directed against lymphohematopoietic cells (lymphohematopoietic GVH reactions, or LGVHR) occur across complete major histocompatibility barriers in mixed chimeras without producing GVHD. This is achieved by administering donor T cells to tolerant mice several weeks or months after mixed chimerism has been established. These LGVHR are manifested as (1) conversion of mixed chimerism to full chimerism and (2) GVL effects. Both LGVHR are due to the GVH alloresponse but occur without GVHD. This LGVHR phenomenon reflects the failure of donor T cells that are activated by host alloantigens presented within the lymphohematopoietic system to migrate into the epithelial GVHD target tissues. Such migration of donor T cells is induced by proinflammatory stimuli, such as those stimuli that are induced by irradiation and chemotherapy used in conditioning regimens, that upregulate molecules in these epithelial GVHD target tissues to allow or promote T cell infiltration. These molecules include chemokines and adhesion molecules. Because LGVHR serves as powerful immunotherapy for lymphohematopoietic malignancies, the ability to exploit this GVH alloresponse without inciting severe GVHD in human mixed chimeras provides a new method to treating lymphohematopoietic malignancies.

The present invention provides a method of blocking molecules that allow T-cell migration into tissues such as epithelial GVHD target tissues. The blockade is achieved with antibodies or other antagonists of chemokines, adhesion molecules, or their receptors, or with drugs that block upregulation of chemokine receptors on donor T cells. This method allows the LGVHR to mediate GVL effects without inducing GVHD. This method is used both in the setting of conventional myeloablative conditioning and with non-myeloablative BMT protocols, and allows the exploitation of the more powerful GVL effects that are achieved with extensively HLA-mismatched BMT.

Preferably, the agent that blocks molecules that allows T cell infiltration into GVHD target tissues in the subject is an antagonist of chemokine function. More preferably, the antagonist of chemokine function is selected from the group consisting of small organic molecules, natural products, peptides, proteins and peptidomimetics. In another preferred embodiment, the antagonist of chemokine function is a protein. In another preferred embodiment of this aspect of the invention, the protein is an anti-chemokine receptor antibody, an anti-chemokine antibody or antigen-binding function thereof. In another preferred embodiment, the agent that blocks molecules that allow T cell infiltration into GVHD target tissues in the subject is an antagonist of an adhesion molecule. Examples of adhesion molecules include, but are not limited to, P-selectin, E-selectin, L-selectin, ICAM-1, VCAM-1, VLA-4, PSGL-1, LFA-1, CD31, and CD44.

The donor cells used in the methods of the invention may be bone marrow cells, purified bone marrow cells, or purified peripheral blood cells. In methods of the invention where donor T cells are introduced, the cell graft may comprise bone marrow cells, purified bone marrow cells, or purified stem cells with an add-back of T-cells.

Preferably, the method includes treating the subject with an immunosuppressive regimen in an amount sufficient to prevent rejection of the donor hematopoietic stem cells and insufficient to prevent a GVH response. More preferably, the method provides that the immunosuppressive regimen includes inactivating or depleting host T lymphocytes and or natural killer (NK) cells in the subject. In another preferred embodiment, the immunosuppressive regimen includes treatment with T cell-depleting anti-CD4 and/or anti-CD8 antibodies. Other preferred embodiments include, an immunosuppressive regimen that includes treatment with one or more of anti-thymocyte globulin (ATG), OKT3, LO-CD2a, MEDI-507.

Other embodiments of this aspect of the invention cover methods wherein the subject is treated with a cytoreductive agent selected from one or more of alkylating agents (e.g., nitrogen mustards, [such as mechloretamine], cyclophosphamide, melphalan and chloambucil), alkyl sulphonates (e.g. busulphan), nitrosoureas (e.g., carmustine, lomustine, semustine and streptoxocine), triazenes (e.g., dacarbazine), antimetabolites (e.g., folic acid analogs such as methotrexate), pyrimidine analogs (e.g., fluorouracil and cytarabine), purine analogs (e.g., fludarainve, idarubicin, cytosine arabinoside, mercapto purine and thioguanine), vinca alkaloids (e.g., vinblastine, vincristine and vendesine), epidophyllotoxins (etoposide and teniposide), antibiotics (dactinomycin, daunorubicin, doxorubicin, bleomycin, plicamycin and mitomycin), dibromomannitol, deoxyspergualin, dimethyl myleran and thiotepa. Preferred methods also include embodiments wherein the immunosuppressive regimen includes treatment with thymic irradiation.

Preferably, the agent that blocks molecules that allow T cell infiltration into GVHD target tissue of the subject is an antagonist of chemokine function. More preferably, the antagonist of chemokine function is selected from the group consisting of small organic molecules, natural products, peptides, proteins and peptidomimetics. Still more preferably, the antagonist of chemokine function is a protein. Another preferred embodiment is a method wherein the protein is an anti-chemokine receptor antibody, anti-chemokine antibody or antigen-binding function thereof. Still other embodiments of this aspect of the invention feature methods wherein, the agent that blocks molecules that allow T cell infiltration into GVHD target tissue of the subject is an antagonist of an adhesion molecule. The inventions also covers methods wherein the donor hematopoietic engraftment is mixed hematopoietic chimerism or full hematopoietic chimerism. Another preferred embodiment covers methods wherein the T cells in the allogeneic hematopoietic cell graft are bone marrow cells, purified bone marrow cells, or purified stem cells with an add-back of T cells.

In methods described herein, the donor is from the same species as the subject, or from a different species. In allogeneic methods the donor of stem cells and the donor of leukocytes should be the same individuals. In xenogeneic methods, the subject is a mammal, preferably a primate and more preferably a human. The donor mammal is, by way of example, a swine, e.g., a miniature swine, or a nonhuman primate. In xenogeneic methods the donor of stem cells and the donor of leukocytes need not be the same individual but is from a different individual which is MHC matched or highly inbred, e.g., inbred miniature swine which are MHC matched.

Methods of the invention allow exploitation of the engraftment-promoting and GVL effects of donor T-cells while minimizing GVHD in HLA-mismatched pairs and in xenogeneic methods, allowing many more subjects to benefit from hematopoietic stem cell transplantation.

GVL effects are mediated by T-cells and other cell types in allogeneic marrow inocula. While GVL effects are often associated with GVHD, these two phenomena are dissociated. One strategy for separating these phenomena is the temporal separation of BMT and donor T-cell infusion. Methods of the invention provide initial conditioning, with a mild, relatively non-toxic and non-myeloablative regimen. The combination of a mild conditioning regimen and the recovery time permitted before administration of donor T-cells allows the use of this approach in older subjects with chronic hematologic malignancies who are otherwise not considered eligible for BMT.

Because of the high precursor frequency of T lymphocytes reacting to allogeneic MHC molecules, the anti-MHC responses in an allogeneic setting result in much more potent and more rapid GVL responses than are observed for MHC-matched BMT. The presence of single HLA antigen mismatches is associated with increased GVL effects in BMT from related donors. Because of the very potency of these anti-MHC responses, and because of the ubiquity of class I MHC expression, GVHD is a major impediment to the full exploitation of this potentially enormous GVL effect. The greater susceptibility of lymphohematopoietic cells than other host tissues to destruction by MHC-specific donor T-cells is due to the immediate contact of donor cells with host cells within the lymphohematopoietic system. Additional inflammatory stimuli, such as cytokines induced by myeloablative conditioning treatments, are required to activate endothelial cells and, in combination with activation-induced increased function of T-cell adhesion molecules, permit T-cell adhesion and migration into GVHD target tissues. Unfortunately, conditioning of subjects for allogeneic BMT, particularly harsh conditioning, activates inflammatory stimuli, thus explaining their exquisite sensitivity to the development of GVHD. Methods of the invention avoid GVHD while preserving the strong lymphohematopoietic GVL effects of mismatched allogeneic or xenogeneic donor tissue without causing GVHD, in part, by the use of conditioning regimens that are less toxic and less pro-inflammatory, followed by delayed administration of donor T-cells. Such a delay allows recovery of host immune resistance to GVHD and/or resolution of the conditioning-induced pro-inflammatory state, and hence decreased susceptibility to GVHD. Since the host conditioning used is not myeloablative, this approach is particularly appropriate for the treatment of chronic leukemias, for which immediate curative cytoreduction need not be attempted.

Bone marrow transplantation has not been widely used for the treatment of CLL, an incurable and ultimately fatal disease, due largely to the fact that this disease often afflicts older subjects who are not considered eligible for allogeneic bone marrow transplantation. Because CLL is a slow-growing leukemia, it is particularly amenable to cure without ablative conditioning when allogeneic T-cells are administered for their GVL effect. Additional chronic hematologic malignancies that often afflict older persons include multiple myeloma, chronic myelogenous leukemia, and low- and intermediate-grade NHLs are amenable to methods of the invention.

Successful allogeneic bone marrow transplantation is often limited by (1) lack of HLA-matched donor (only 25-30% of subjects will have an HLA-phenotypically-identical sibling) and for subjects who do undergo an allogeneic BMT, (2) substantial treatment-related mortality, particularly in patients ≧40 years of age, and (3) disease relapse. Methods of the invention expand the availability of transplantation by allowing transplants from HLA-mismatched donors and xenogeneic donors, improve the safety profile of BMT, and enhance the graft-versus-malignancy effects of mismatched transplantation. Methods of the invention provide a number of advantages. First, a moderate dose of cyclophosphamide, a dose of 200 mg/kg, is not myeloablative and is associated with less regimen-related morbidity and mortality than conventional transplant preparative regimens. Post-chemotherapy hematopoietic recovery is expected in approximately 2 weeks following drug administration. While the decreased aggressiveness of the chemotherapy also means less tumor cell kill, the decreased cytoreductive effect of chemotherapy will be outweighed by an enhanced graft-versus-malignancy effect. Second, the non-myeloablative conditioning regimen and the presumably lower likelihood of graft-versus-host disease will allow for treatment of subjects of older age than are considered for conventional allogeneic BMT.

Thus, methods of the invention provide for: less toxic conditioning, which induces less host damage and less pro-inflammatory response to conditioning; partial depletion of donor T cells by administration to the subject of T cell inhibiting treatment, e.g., anti-T cell antibodies; and minimization of GVHD by delaying donor leukocyte administration until the pro-inflammatory environment created by conditioning has receded. Methods of the invention allow the use of hematopoietic stem cells from mismatched, or xenogeneic, donors, and thus provide increased GVL activity and increases the number of individuals who receive hematopoietic stem cell therapy for hematologic malignancies.

Methods of the invention also provide for the treatment of non-neoplastic disorders or a hemoglobinopathies, e.g., sickle cell anemia, aplastic anemia, thalassemia, or similar disorders.

Treatment of Hematologic Disorders

In general, the invention features, in a first aspect, a method of treating a subject e.g., a human, having a hematologic disorder, e.g., a hematologic malignant disorder, e.g., leukemia. The method includes administering donor hematopoietic stem cells under conditions which minimize GVDH and maximize GVL, thereby treating the disorder, e.g., relieving or alleviating one or more symptoms of the disorder.

In methods described herein, the donor is from the same species as the subject, or from a different species. In allogeneic methods the donor of stem cells and the donor of leukocytes should be the same individuals. In xenogeneic methods, the subject is a mammal, preferably a primate and more preferably a human. The donor mammal is, by way of example, a swine, e.g., a miniature swine, or a nonhuman primate. In xenogeneic methods the donor of stem cells and the donor of leukocytes need not be the same individual but is from a different individual which is MHC matched or highly inbred, e.g., inbred miniature swine which are MHC matched.

While not wishing to be bound by theory, the myeloreductive non-myeloablative treatment is believed to prepare the subject for the induction of mixed chimerism and has a cytoreductive effect on cancer cells. The myeloreductive nonmyeloablative treatment should be administered prior to introduction of the donor hematopoietic stem cells, preferably sufficiently prior to the administration of donor hematopoietic stem cells such that if it includes the administration of a chemical agent, the chemical agent will be cleared from the circulatory system prior to the administration of donor hematopoietic stem cells.

Preferred myeloreductive non-myeloablative agents are alkylating agents, e.g., cyclophosphamide, or fludarabine or similar substances, however, hematopoietic space creating antibodies or drugs, e.g., inhibitors of cell proliferation, e.g., DSG, or an anti-metabolite, e.g. brequinar, or an anti-T cell antibody, e.g., one or both of an anti-CD4 or anti-CD8 antibody is used as a myeloreductive non-myeloablative agent.

In preferred embodiments, the myeloreductive non-myeloablative treatment is sufficiently mild that at least 10, and more preferably at least 30, 50, or 75% of the subjects to which it is administered will form mixed chimeras (as opposed to having their bone marrow totally ablated).

In preferred embodiments, immune cell activity, e.g., T cell activity, preferably graft reactive T cell activity, is inhibited in the subject. While not wishing to be bound by theory, the inhibition of T cells is believed to prepare the subject for the induction of mixed chimerism by inhibition of subject T cell activity which would mount an immune response against the donor hematopoietic stem cells and to inhibit donor T cell activity which would mount an immune response against the subject (GVHD).

Numerous methods of inhibiting T cell activity are suitable for use in methods described herein. By way of example, these include:

the administration of anti-T cell antibodies, e.g., an ATG preparation, polyclonal or monoclonal antibody directed against CD4, CD8, or CD2 (an anti-CD2 antibody, e.g., the anti-CD2 monoclonal antibody BTI-322 or a humanized version thereof, or an antibody which overlaps or binds the epitope recognized by BTI-322, are particularly useful);

the administration of an agent, e.g., an antibody, which blocks or otherwise inhibits a pathway, e.g., a costimulatory pathway, of T cell activation (agents, e.g., antibodies, which block the CD28-B7 pathway, e.g., a CTLA4-IgG fusion protein, or agents, e.g., an antibody which blocks the CD40-gp39 pathway, e.g., an anti-gp39 antibody, are particularly suited for use in the method), or generally, by the administration of a treatment which down modulates or otherwise inhibits one or more of the T cell receptor, CD4 co-receptor, CD8 co-receptor or other receptor or co-receptor which promotes T cell activation or maturation;

the administration of an immunosuppressive agent, e.g., cyclosporine, FK506, or rapamycin; and the administration of thymic irradiation, or other treatment which creates thymic space.

Treatments which inhibit T cell activity are administered at any time in the course of the method but should not be such that donor T cells will be entirely eliminated. Treatments are administered prior to, at the same time as, or after, the administration of donor hematopoietic stem cells. Preferably, such treatments are provided both before and after the administration of donor hematopoietic stem cells. Treatment prior to the administration of donor hematopoietic stem cells is believed desirable in that it will condition the subject for the receipt of the donor hematopoietic stem cells. Treatment after the administration of donor hematopoietic stem cells is believed desirable in that it will reduce donor-immune attack on the host and further promote acceptance by the subject of the donor hematopoietic stem cells.

For best results, treatments to inhibit T cell activity, e.g., anti-T cell antibodies or cyclosporine, are administered repeatedly. For example, such treatment is administered one, two, three, or more times prior to donor bone marrow transplantation. Typically, a pre-stem cell treatment, e.g., the administration of antibodies, will be given to the subject about 1, 2, 3, 4, or 5 days prior to stem cell transplantation. It is desirable to repeat pre-stem cell administrations every 1-5 days until the subject shows excess antibodies in the serum and about 80, 90, or 99% depletion of peripheral T cells and then to perform the stem cell transplantation. Treatments are also administered one, two, three, or more times after donor hematopoietic stem cell transplantation. Typically, a post-stem cell transplant treatment will be given about 1, 2, 3, 4, or 5 days after bone marrow transplantation.

In preferred embodiments two or more T cell inhibiting modalities or treatments are combined. In particularly preferred embodiments, an antibody, e.g., an anti-T cell antibody, an immunosuppressive agent, e.g., cyclosporine, and thymic irradiation, are all administered to the subject. An agent is administered once, or more than once, but the administrations should be short term and not chronic or long term administration. In general, this will mean the treatment is administered for not more than 30, 45, 60, 90, or 120 days, and in many treatments this means administration on 1, 2, 3, 4, 5, or fewer days. Cyclosporine and similar agents will generally be administered for not more than 30, 45, 60, 90, or 120 days. Antibodies will generally be administered for 1, 2, 3, 4, 5, or fewer days.

While not wishing to be bound by theory, the donor hematopoietic stem cells are believed to provide hematologic function, and to induce tolerance to donor antigen, so as to reduce the subject response to any subsequent donor tissue, e.g., a donor leukocyte infusion, which is administered.

In preferred embodiments, mixed chimerism is induced in the subject and the state of mixed chimerism is formed in the absence of hematopoietic space created by space creating irradiation, e.g., whole body irradiation.

In preferred embodiments, donor leukocytes are administered to the subject. While not wishing to be bound by theory, the donor leukocyte administration is believed to provide additional GVL activity—donor leukocytes are believed to further and very effectively reduce the number of cancer cells in the subject. The need for or appropriateness of donor leukocyte administration is evidenced by a lack of increase in donor chimerism, lack of GVHD symptoms, or incomplete tumor regression. Donor leukocyte administration should be delayed for at least 10, 20, 30, 35 or 60 days after the administration of any myeloreductive non-myeloablative or other space creating treatment. Initial trials showed a delay of about 35 days to be suitable. The donor leukocyte infusion is delayed to avoid introduction of relatively large numbers of donor immune cells into the host during the period in which the space creating treatment has induced pro-inflammatory conditions. Delay allows the host to recover from conditioning and to be less susceptible to GVHD, especially when mismatched donor tissue is used. The donor leukocyte infusion converts the mixed chimeric state of the subject to one which is fully chimeric, but, the graft cell mediated immune attack will be limited to the hematopoietic compartment; thereby minimizing GVHD and maximizing GVL effects.

In preferred embodiments the method includes creating thymic space in the subject. Thymic space is created, e.g., by irradiating the thymus of the subject, e.g., by administering between 100 and 1,000, more preferably between 300 and 700, e.g., 700 rads, of thymic irradiation, or by administering anti-T cell antibodies in sufficient dose to inactivate thymocytes. Other methods for the creation of thymic space include: the administration of steroids, corticosteroids, brequinar, or an immune suppressant chemical or drug, e.g., rapamycin, cyclosporin, or FK506. An effective treatment should deplete single positive thymocytes to an extent that engraftment and the formation of mixed chimerism is optimized. In preferred embodiments the subject's single positive thymocytes are depleted by at least 20, 40, 60, or 80%. Treatments which result in between 10 and 90% depletion are preferred.

In preferred embodiments the subject does not receive additional treatments which stimulate the release of a cytokine by mature T cells. For example, the subject should not receive a substance, e.g., a steroid drug, e.g., Prednisone (17,21-dihydroxypregna-1,4-diene-3,11,20-trione), at a dosage or concentration which stimulates the release of a cytokine by mature T cells in the subject. Preferably, the subject is free of such treatment from the time stem cells are first administered until mixed chimerism is established or donor leukocytes administered.

Preferred embodiments include the administration of an agent, e.g., 15-deoxyspergualin, mycophenolate mofetil, brequinar sodium, or a similar agent, which inhibits the production, levels, or activity of antibodies in the subject.

In preferred embodiments, particularly xenogeneic methods, the method includes: inhibiting natural killer cells of the subject preferably prior to introducing donor tissue into the subject, e.g., by introducing into the subject an antibody capable of binding to natural killer cells of the subject.

One source of anti-NK antibody is anti-human thymocyte polyclonal anti-serum. A second anti-mature T cell antibody is administered as well, which inhibits T cells as well as NK cells. Anti-T cell antibodies are present, along with anti-NK antibodies, in anti-thymocyte anti-serum. Repeated doses of anti-NK or anti-T cell antibody is preferable. Monoclonal preparations are used in the methods of the invention.

In preferred embodiments, particularly xenogeneic embodiments, the method includes administering donor species stromal cells or administering donor specific growth factors or cytokines, e.g., SCF or GM-SGF. Where the donor is a miniature swine, the method includes administering one or more of swine SCF, swine IL-3, or swine GM-SCF, to the subject. The method further includes the step of administering a first or subsequent dose of a cytokine or growth factor to the subject: when the subject begins to show signs of rejection; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells.

In preferred embodiments, particularly xenogeneic embodiments, the method includes the step of, preferably prior to hematopoietic stem cell transplantation, inhibiting natural subject antibodies, e.g., by depleting natural antibodies from the blood of the subject. Depletion is achieved, by way of example, by contacting the subject's blood with an epitope which absorbs preformed anti-donor antibody. The epitope is coupled to an insoluble substrate and provided, e.g., as an affinity column. For example, an α1-3 galactose linkage epitope-affinity matrix, e.g., matrix bound linear B type VI carbohydrate, is used to deplete natural antibodies. Depletion is also achieved by hemoperfusing an organ, e.g., a liver or a kidney, obtained from a mammal of the donor species. (In organ hemoperfusion antibodies in the blood bind to antigens on the cell surfaces of the organ and are thus removed from the blood.) Other methods for depleting or otherwise inactivating natural antibodies are used with the methods described herein. For example, drugs which deplete or inactivate natural antibodies, e.g., deoxyspergualin (DSG) (Bristol), or anti-IgM antibodies, are administered to the recipient of an allograft or a xenograft. One or more of, DSG (or similar drugs), anti-IgM antibodies, and hemoperfusion, is used to deplete or otherwise inactivate subject natural antibodies in methods of the invention.

In preferred embodiments: the donor of the hematopoietic stem cell and the donor leukocytes is the same individual. In other preferred embodiments, particularly xenogeneic embodiments, the donor of the hematopoietic stem cell and the donor leukocytes are different individuals, e.g., different individuals which are MHC identical.

Although methods of the invention generally reduce or eliminate the need for myeloablative conditioning, some embodiments include the step of, prior to hematopoietic stem cell transplantation, creating hematopoietic space for the induction of mixed chimerism by irradiating the subject with low dose, e.g., less than 400, preferably less than 300, more preferably less than 200 or 100 rads, whole body irradiation to partially deplete the bone marrow of the subject. The level of such treatment will be very substantially lower than that used in lethal conditioning. As is discussed herein, this treatment is reduced or entirely eliminated.

Achievement of Lymphohematopoietic GVH Reactions Without GVHD in Established Mixed Allogeneic Chimeras Recent studies in rodent models have shown that engraftment of MHC-mismatched allogeneic marrow is achieved in recipients conditioned with relatively non-toxic, non-myeloablative regimens (Sharabi, et al., *J. Exp. Med.,* 169:493-502 (1989)); (Tomita, et al., *Transplantation,* 61:469-477 (1996)); (Sykes, et al., *Nature Med.,* 3:783-787 (1997)). Because host hematopoietic cells are not ablated in these models, donor stem cell engraftment leads to a permanent state of mixed hematopoietic chimerism, in which donor and host-derived hematopoietic elements coexist. Mixed chimerism has also been achieved in several large animal models involving non-myeloablative conditioning, including MHC-identical dogs receiving BMT after sublethal irradiation and pharmacological immunosuppressive therapy (Storb, et al., *Blood,* 89:3048-3054 (1997)). Transient mixed chimerism has been achieved across MHC barriers in monkeys conditioned with a regime based on our non-myeloablative mouse protocol (Kawai, et al., *Transplantation,* 59:256-262 (1995)), in which anti-T cell mAbs are used as the major agent to overcome host resistance to alloengraftment (Sharabi, et al., *J. Exp. Med.,* 169:493-502 (1989)). The conditioning used in these models is much less toxic than lethal total body irradiation (TBI).

In the mouse model it was demonstrated that, if sufficient time is allowed to pass after conditioning and BMT, hematopoietic chimeras produced across MHC barriers are resistant to GVHD induction by donor leukocyte infusions (DLI) containing large numbers of non-tolerant donor T cells. Lethally irradiated mice showed the development of some degree of resistance to GVHD between day 0 and day 8 (Sykes, et al., *Transplantation,* 46:327-330 (1988)). Similar results have subsequently been obtained by other groups (Johnson, et al., *Bone Marrow Transplant,* 11:329-336 (1993)); (Xun, et al., *Transplantation,* 64:297-302 (1997)), and the administration of delayed DLI to allogeneic chimeras was shown to mediate GVL effects without causing GVHD (Johnson, et al., Bone Marrow Transplant, 11:329-336 (1993)). In addition, the complication of GVHD has been less severe than expected when large numbers of donor T cells have been administered to humans for the treatment of relapsed chronic myelogenous leukemia (and with less success for other leukemias) following previous BMT (Kolb, et al., *Blood,* 86:2041-2050 (1995)); (Slavin, et al., *Blood,* 87:2195-2204 (1996)); (van Rhee, et al., *Blood,* 83:3377-3383 (1994)). Furthermore, the incidence of GVHD was reduced by delaying the time between cyclophosphamide administration and transplantation of HLA-mismatched marrow to subjects with severe combined immunodeficiencies (Lehnerts, et al., *Bone Marrow Transplant,* 13:473-477 (1994)). These results suggest that, as in mice, GVHD resistance also increases with time after conditioning in humans.

Accordingly, studies by the inventor in fully MHC-mismatched murine mixed hematopoietic chimeras have led to the demonstration that despite their failure to induce GVHD, DLI mediate powerful lymphohematopoietic graft-versus-host reactions. Delayed administration of DLI to mixed chimeras results in the elimination of all host hematopoietic cells, so that mixed chimeras are converted to fully allogeneic chimeras (Sykes, et al., *J. Exp. Med.,* 168:2391-2396 (1988)) (M.-G. Wang and M. Sykes, unpublished data). An anti-T cell mAb-based non-myeloablative regimen to include a high dose of cyclophosphamide treatment prior to BMT in place of low-dose (3 Gy) TBI. Chimeras prepared in this manner are also resistant to the induction of GVHD, while powerful LGVHR convert mixed chimeras to full chimeras. The greater susceptibility of lymphohematopoietic cells than other host tissues to destruction by MHC-reactive allogeneic donor T cells is due to the immediate contact of donor T cells with host hematopoietic cells within the lymphohematopoietic system.

Preferably, the agent that blocks molecules that allow T cell infiltration into GVHD target tissues in the subject is an antagonist of chemokine function. More preferably, the antagonist of chemokine function is selected from the group consisting of small organic molecules, natural products, peptides, proteins and peptidomimetics. In another particularly preferred embodiment, the antagonist of chemokine function is a protein. In another preferred embodiment of this aspect of the invention, the protein is an anti-chemokine receptor antibody, an anti-chemokine antibody or antigen-binding function thereof. Other embodiments of this aspect cover methods wherein the agent that blocks molecules that allow T cell infiltration into GVDH target tissues in the subject is an antagonist of an adhesion molecule. The adhesion molecules are, preferably, P-selectin, E-selectin, ICAM-1, VCAM-1, VLA-4, PSGL-1, and LFA-1. Preferably, the method includes methods wherein the T cells in the allogeneic hematopoietic cell graft are bone marrow cells, purified bone marrow cells, or purified stem cells with an add-back of T cells.

Preferably, the method includes treating the subject with an immunosuppressive regimen in an amount sufficient to prevent rejection of the donor hematopoietic stem cells and insufficient to prevent a graft-versus-host response. More preferably, the method provides that the immunosuppressive regimen includes inactivating or depleting host T lymphocytes and or natural killer (NK) cells in the subject. In another particularly preferred embodiment, the immunosuppressive regimen includes treatment with T cell-depleting anti-CD4 and/or anti-CD8 antibodies.

Other preferred embodiments include, an immunosuppressive regimen that includes treatment with one or more of anti-thymocyte globulin (ATG), OKT3, LO-CD2a, MEDI-507. Other embodiments of this aspect of the invention cover methods wherein the myeloreductive treatment includes treating the subject with a cytoreductive agent selected from one or more of alkylating agents (e.g., nitrogen mustards, [such as mechloretamine], cyclophosphamide, melphalan and chloambucil), alkyl sulphonates (e.g. busulphan), nitrosoureas (e.g., carmustine, lomustine, semustine and streptoxocine), triazenes (e.g., dacarbazine), antimetabolites (e.g., folic acid analogs such as methotrexate), pyrimidine analogs (e.g., fluorouracil and cytarabine), purine analogs (e.g., fludarainve, idarubicin, cytosine arabinoside, mercapto purine and thioguanine), vinca alkaloids (e.g., vinblastine, vincristine and vendesine), epidophyllotoxins (etoposide and teniposide), antibiotics (dactinomycin, daunorubicin, doxorubicin, bleomycin, plicamycin and mitomycin), dibromomannitol, deoxyspergualin, dimethyl myleran and thiotepa. Preferred methods also include embodiments wherein the immunosuppressive regimen includes treatment with thymic irradiation.

In other preferred embodiments, the agent that blocks molecules that allow T cell infiltration into GVHD target tissue of the subject is an antagonist of chemokine function. More preferably, the antagonist of chemokine function is selected from the group consisting of small organic molecules, natural products, peptides, proteins and peptidomimetics. Still more preferably, the antagonist of chemokine function is a protein. Another preferred embodiment is a method wherein the protein is an anti-chemokine receptor antibody, an anti-chemokine antibody or antigen-binding function thereof. Still other embodiments of this aspect of the invention feature methods wherein, the agent that blocks molecules that allow T cell infiltration into GVHD target tissue of the subject is an antagonist of an adhesion molecule. More preferably, the method encompass wherein the donor hematopoietic engraftment is mixed hematopoietic chimerism or full hematopoietic chimerism. Preferably, the method includes those methods wherein the T cells in the allogeneic hematopoietic cell graft are bone marrow cells, purified bone marrow cells, or purified stem cells with an add-back of T cells.

Results in mixed chimeras demonstrate clearly that a graft-versus-host reaction in itself is insufficient to cause GVHD (Sykes, et al., *J. Exp. Med.,* 168:2391-2396 (1988)). Additional inflammatory stimuli, such as those induced by conditioning, are required to activate or promote endothelial cells, tissue parenchymal cells and T cells to a state that permits T cell adhesion and migration into GVHD target tissues. Migration of T cells into target tissues where they affect GVHD-associated injury is likely to be highly dependent not only on the activation of T cells by antigen, as occurs in a LGVHR, but also on the upregulation of cytokines, chemokines, and adhesion molecules by small vessels in the target tissues.

T cell migration into the tissues is a multi-step process progressing from leukocyte rolling within the vessel, activation of leukocyte integrins, tight adhesion to endothelial cells via activated integrins, and diapedesis. The latter three events in this sequence depend on the expression by endothelial cells and tissue parenchymal cells of molecules that are upregulated by toxic conditioning regimens. Lethal irradiation, for example, has been associated with the production of the proinflammatory cytokines IL-1, IL-6 and TNF-a (Xun, et al., *Blood,* 83:2360-2367 (1994)); (Krivenko, et al., *Int. J. Hematol,* 55:127 (1992)), which upregulate the expression of the endothelial cell adhesion molecules E-selectin, P-selectin, ICAM-1 and VCAM-1 (Carlos, et al., *Blood,* 84:2068-2101 (1994)); (Pober, et al., *J. Immunol,* 138:3319 (1987)), all of which are expressed on endothelial cells of non-lymphoid tissues and facilitate the migration of circulating T cells into these tissues. Cytoxan also induces proinflammatory cytokine production, though in lower amounts than TBI (Xun, et al., *Blood,* 83:2360-2367 (1994)); (Schwaighofer, et al., *Transplantation,* 62:947-953 (1996)). In addition to its expression on endothelial cells, ICAM-1 is also expressed on epithelial cells, and, by being an important ligand for the β2 integrin LFA-1 on CTL, plays a role in the direct destruction of epithelial cells in GVHD. This molecule also plays an essential role in antigen presentation to T cells, as APC from ICAM-1-knockout mice have markedly deficient stimulating activity in mixed lymphocyte reactions (Sligh, Jr., et al., *Proc. Natl. Acad. Sci. USA*, 90:8529-8533 (1993)). Blockade of the LFA-1/ICAM-1 adhesion pathway has been shown to contribute to GVHD inhibition in combination with blockade of the B7/CD28 pathway in a mouse model (Blazar, et al., *Blood*, 85:2607-2618 (1995)). Of note, upregulation of ICAM-1 and VCAM-1 has been observed on tissue epithelial cells of humans with intestinal and cutaneous GVHD (Norton, et al., *Transplantation*, 51:1203-1206 (1991)); (Norton, et al., *Clin. Exp. Immunol.*, 87:231-236 (1992)); (Norton, et al., *J. Clin. Pathol.*, 44:586-591 (1991)). E- and P-selectins play an especially important role in the recruitment of Th1 cells, which are implicated in acute GVHD pathogenesis (De Wit, et al., *J. Immunol.*, 150:361-366 (1993)); (Allen, et al., *Eur. J. Immunol.*, 23:333-337 (1993)); (Via, et al., *J. Immunol.*, 153:4040-4047 (1994)); (Szebeni, et al., *Transplantation*, 58:1385-1393 (1994)), into inflamed tissues (Austrup, et al., *Nature*, 385:81-83 (1997)). In addition to adhesion molecules, a growing number of chemokines, which are low molecular weight proteins that attract leukocytes to sites of inflammation, have been shown to play an important role in allowing T cell entry into tissues.

Methods of the invention are used to treat hematologic disorders. A hematologic disorder is a disorder in which there is a malfunction in the subject's hematopoietic cells, e.g., the hematopoietic stem cells, which are treated by replacing or supplementing the subject's hematopoietic stem cells. Hematologic disorders include disorders having unwanted cell proliferation e.g., hematologic cancers, e.g., hematopoietic and lymphoid malignancies e.g., leukemia, e.g., chronic lymphocytic leukemia (CLL) and other chronic hematologic malignancies, including multiple myeloma, chronic myelogenous leukemia, and low- and intermediate-grade non-Hodgkin's lymphomas. Hematologic disorders also include, non-neoplastic disorders and hemoglobinopathies, e.g., sickle cell anemia, aplastic anemia, thalassemia, and similar disorders.

As used herein, "myeloablative" refers to a treatment in which death, due to marrow failure, in a significant number of recipients, will occur if hematopoietic stem cell transplantation is not given.

As used herein, "non-myeloablative" refers to a treatment which kills marrow cells but will not, in a significant number of recipients, lead to death from marrow failure.

As used herein, "myeloreductive", refers to a treatment which causes cytopenia or anemia.

"Subject", as used herein, refers to a mammal, e.g., a human.

"Discordant species combination", as used herein, refers to two species in which hyperacute rejection occurs when a graft is grafted from one to the other. Generally, discordant species are from different orders, while non-discordant species are from the same order. For example, rats and mice are non-discordant concordant species. Concordant species combinations do not exhibit hyperacute rejection. In xenogeneic method of the invention, the donor and recipient (subject) are a discordant or non-discordant species combination.

"Miniature swine", as used herein, refers to a miniature pig which is preferably wholly or partially inbred at least one MHC locus. The coefficient of inbreeding of the herd which supplies the miniature swine should be at least 0.70 and more preferably at least 0.82. The herd from which donor animals are drawn should be homozygous at the SLA genes.

"Stromal tissue", as used herein, refers to the supporting tissue or matrix of an organ, as distinguished from its functional elements or parenchyma.

"Hematopoietic space", as used herein, refers to a condition created in the bone marrow which promotes engraftment of administered stem cells. In the art, hematopoietic space has often been created by irradiation of the bone marrow with whole body irradiation, but the methods of the invention generally use nonmyeloablative treatments.

"Hematopoietic stem cell", as used herein, refers to a cell, e.g., a bone marrow cell, or a fetal liver or spleen cell, which is capable of developing into all myeloid and lymphoid lineages and by virtue of being able to self-renew provides long term hematopoietic reconstitution. Purified preparations of hematopoietic cells or preparations, such as bone marrow, which include other cell types, are used in methods of the invention. Although not wishing to be bound by theory, it is believed that the hematopoietic stem cells home to a site in the recipient. The preparation should include immature cells, i.e., undifferentiated hematopoietic stem cells; these desired cells are separated out of a preparation or a complex preparation are administered. For example, in the case of bone marrow stem cells, the desired primitive cells are separated out of a preparation or a complex bone marrow sample including such cells are used. Hematopoietic stem cells are from fetal, neonatal, immature or mature animals. Stem cells derived from the cord blood of the recipient or the donor are used in methods of the invention. See U.S. Pat. No. 5,192,553, hereby incorporated by reference, and U.S. Pat. No. 5,004,681, hereby incorporated by reference.

An "immunosuppressive agent", as used herein, is an agent, e.g., a chemical agent, e.g., a drug, which, when administered at an appropriate dosage, results in the inhibition of T cells. Examples of such agents are cyclosporine, FK-506, and rapamycin.

"Thymic" or "lymph node" or "thymocytes" or "T cell", as used herein, refers to thymocytes or T cells which are resistant to inactivation by traditional methods of T cell inactivation, e.g., inactivation by a single intravenous administration of anti-T cell antibodies, e.g., anti-bodies, e.g., ATG preparation.

"Thymic irradiation", as used herein, refers to a treatment in which least 20, and preferably at least 50, 75, 90, or 95% of the administered irradiation is targeted to the thymus. Whole body irradiation, even if the thymus is irradiated in the process of delivering the whole body irradiation is not considered thymic irradiation.

"MHC antigen", as used herein, refers to a protein product of one or more MHC genes; the term includes fragments or analogs of products of MHC genes which evoke an immune response in a recipient organism. Examples of MHC antigens include the products (and fragments or analogs thereof) of the human MHC genes, i.e., the HLA genes.

"Hematopoietic space-creating irradiation", as used herein, refers to irradiation directed to the hematopoietic tissue, i.e., to tissue in which stem cells are found, e.g., the bone marrow. It is of sufficient intensity to kill or inactivate a substantial number of hematopoietic cells. It is often given as whole body irradiation.

"Thymic space" as used herein, is a state created by a treatment that facilitates the migration to and/or development in the thymus of donor hematopoietic cells of a type which deletes or inactivates host thymocytes that recognize donor antigens. It is believed that the effect is mediated by elimination of host cells in the thymus.

"Tolerance", as used herein, refers to an inhibition of a graft recipient's immune response which would otherwise occur, e.g., in response to the introduction of a nonself MHC antigen into the recipient. Tolerance involves humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Tolerance, as used herein, refers to a donor antigen-specific inhibition of the immune system as opposed to the broad spectrum inhibition of the immune system seen with immunosuppressants. Tolerance is the ability of the graft to survive in an MHC mismatched or xenogeneic recipient without chronic immunosuppression.

"Inhibiting immune cell activity" refers to reducing the number of active immune cells, e.g., thymocytes, T cells, B cells, or NK cells, preferably donor reactive cells, or precursor donor reactive cells, in a subject. Inhibition includes partial inhibition, or partial reduction (as opposed to total elimination) of the number of active immune cells, e.g., T cells.

As used herein, "chemokines" refer to a family of proinflammatory mediators that promote recruitment and activation of multiple lineages of leukocytes (e.g., lymphocytes, macrophages). They are released by many kinds of tissue cells after activation. Continuous release of chemokines at sites of inflammation mediate the ongoing migration and recruitment of effector cells to sites of chronic inflammation. The chemokines are related in primary structure and share four conserved cysteines, which form disulfide bonds. Based upon this conserved cysteine motif, the family may be divided into distinct branches, including the C—X—C chemokines ($\alpha$-chemokines) and the C—C chemokines ($\beta$-chemokines), in which the first two conserved cysteines are separated by an intervening residue, or are adjacent residues, respectively. (Baggiolini, et al., 1994, *Immunology* 15:127).

The "C—X—C chemokines", as used herein, include a number of potent chemoattractants and activators of neutrophils. These chemokines interleukin-8 (IL-8), PF4, lymphotactin (Kelner, et al., *Science* 266:1395-1399 (1995)), neutrophil-activating peptide-2 (NAP-2), IP-10, and Mig. The "C—C chemokines", as used herein, include, for example, lymphoactin, the macrophage inflammatory proteins MIP-1$\alpha$, MIP-1$\beta$, MIP-1$\gamma$, eotaxin and human monocyte chemotactic proteins MCP's (1 through 5), and RANTES (Regulated on Activation, Normal T Expressed and Secreted, reviewed in [48]), all of which induce the extravasation of activated and memory T cells into the tissues. Recently, several chemokines have been shown to be capable of selectively activating integrins on memory-type but not naive CD4 T cells, thereby augmenting adhesion to ICAM-1 [49]. Activation of lymphocyte integrins such as LFA-1 and VLA-4 is important in arresting rolling leukocytes by permitting their tight adhesion to endothelial cells. While little information is available on the possible role of these chemokines in GVHD, they have been detected in organ grafts undergoing rejection in humans and animals models [50-53].

"Chemokine receptors", as used herein, are members of a superfamily of G protein-coupled receptors (GPCR) which share structural features that reflect a common mechanism of action of signal transduction. (Gerard, et al., 1994, *Ann. Rev. Immunol.* 12:775; Gerard, et al., 1994, *Curr. Opin. Immunol.* 6:140.) Conserved features include seven hydrophobic domains spanning the plasma membrane, which are connected by hydrophilic regions being more diverse. The receptors for the C—C chemokines include: CCR1 which binds for example, MIP-1$\alpha$, RANTES, MCP-2, MCP-3, MCP-4, CKbeta8, CKbeta8-1, leukotactin-1, HCC-1, and MPIF-1; CCR2 which binds, for example, MCP-1, MCP-2, MCP-3 and MCP-4; CCR3 which binds, for example, eotaxin, eotaxin-2, RANTES, MCP-2, MCP-3 and MCP-4; CCR4 which binds, for example, TARC, RANTES, MIP-1$\alpha$ and MCP-1; CCR5 which binds, for example, MIP-1$\alpha$, RANTES, and MIP-1$\beta$; CCR6 which binds, for example, LARC/MIP-3$\alpha$/exodus; CCR7 which binds, for example, ELC/MIP-3$\beta$ and CCR8 which binds, for example, I-309. (Baggiolini, 1998, *Nature* 392:565; Luster, 1998, *New England Journal of Medicine* 338:436; Tsou, 1998, *J. Exp. Med.* 188:603; Nardelli, 1999, *J. Immunol.* 162:435; Youn, et al., 1998, *Blood* 91:3118; and Youn, et al., 1997, *J. Immunol.* 159:5201.)

Chemokine Antagonists

As used herein, the term "antagonist of chemokine function" or "chemokine antagonist" refers to an agent (e.g., a molecule or a compound) which inhibits one or more functions of a chemokine. For example, a chemokine antagonist is an antagonist selected from the group consisting of small organic molecules, natural products, peptides, proteins and peptidomimetics. The chemokine antagonist may, for example, be an antagonist of a chemokine receptor, such as CCR1, and can inhibit the binding of one or more ligands (e.g., MIP-1$\alpha$, RANTES, MCP-2, MCP-3, MCP-4, CKbeta8, CKbeta8-1, leukotactin-1, HCC-1, MPIF-1) to a chemokine receptor and/or inhibit signal transduction mediated through a chemokine receptor (e.g, GDP/GTP exchange by CCR1 associated G proteins, intracellular calcium flux). Accordingly, chemokine receptor-mediated processes and cellular responses (e.g., proliferation, migration, chemotactic responses, secretion or degranulation) can be inhibited with an antagonist of chemokine function.

Preferably, the antagonist of chemokine function is a compound which is, for example, a small organic molecule, natural product, protein (e.g., antibody, chemokine, cytokine), peptide or peptidomimetic. Several molecules that can antagonize one or more functions of chemokine receptors (e.g., CCRI) are known in the art, including the small organic molecules disclosed in, for example, international patent application WO 97/24325 by Takeda Chemical Industries, Ltd.; WO 98/38167 by Pfizer, Inc.; WO 97/44329 by Teijin Limited; WO 98/04554 by Banyu Pharmaceutical Co., Ltd.; WO 98/27815, WO 98/25604, WO 98/25605, WO 98/25617 and WO 98/31364 by Merck & Co., Inc.; WO 98/02151 and WO 99/37617, by LeukoSite, Inc.; WO 99/37651 and WO 99/37619 by LeukoSite, Inc., et al.; U.S. Provisional Patent Application No. 60/021,716, filed Jul. 12, 1996; U.S. patent application Ser. Nos. 09/146,827 and 09/148,236, filed Sep. 4, 1998; Hesselgesser et al., *J. Biol. Chem.* 273(25):15687-15692 (1998); and Howard et al., *J. Medicinal Chem.* 4j(13): 2184-2193 (1998); proteins, such as antibodies (e.g., polyclonal sera, monoclonal, chimeric, humanized) and antigen-binding fragments thereof (e.g., Fab, Fab', F(abl, Fv), for example, those disclosed in Su et al., *J. Leukocyte Biol.* 60:658-656 (1996); chemokine mutants and analogues, for example, those disclosed in U.S. Pat. No. 5,739,103 issued to Rollins et al., WO 96/38559 by Dana Farber Cancer Institute and WO 98/06751 by Research Corporation Technologies, Inc.; peptides, for example, those disclosed in WO 98/09642 by The United States of America. The entire teachings of each of the above cited patent applications and references is incorporated herein by reference.

Antagonists of chemokine function can be identified, for example, by screening libraries or collections of molecules, such as, the Chemical Repository of the National Cancer Institute (U.S.A.), as described herein or using other suitable methods.

Another source of antagonists of chemokine function are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods, such as the methods described herein.

The term "natural product", as used herein, refers to a compound which can be found in nature, for example, naturally occurring metabolites of marine organisms (e.g., tunicates, algae) and plants and which possess biological activity, e.g., can antagonize chemokine function. For example, lactacystin, paclitaxel and cyclosporin A are natural products which can be used as anti-proliferative or immunosuppressive agents.

Natural products can be isolated and identified by suitable means. For example, a suitable biological source (e.g., vegetation) can be homogenized (e.g., by grinding) in a suitable buffer and clarified by centrifugation, thereby producing an extract. The resulting extract can be assayed for the capacity to antagonize chemokine function, for example, by the assays described herein. Extracts which contain an activity that antagonizes chemokine function can be further processed to isolate the chemokine antagonist by suitable methods, such as, fractionation (e.g., column chromatography (e.g., ion exchange, reverse phase, affinity), phase partitioning, fraction crystallization) and assaying for biological activity (e.g., antagonism of chemokine activity). Once isolated the structure of a natural product can be determined (e.g., by nuclear magnetic resonance (NMR)) and those of skill in the art can devise a synthetic scheme for synthesizing the natural product. Thus, a natural product can be isolated (e.g., substantially purified) from nature or can be fully or partially synthetic. A natural product can be modified (e.g., derivatized) to optimize its therapeutic potential. Thus, the term "natural product", as used herein, includes those compounds which are produced using standard medicinal chemistry techniques to optimize the therapeutic potential of a compound which can be isolated from nature.

The term "peptide" as used herein, refers to a compound consisting of from about two to about ninety amino acid residues wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). A "peptide" can comprise any suitable L- and/or D-amino acid, for example, common α-amino acids (e.g., alanine, glycine, valine), non-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are know in the art and are disclosed in, for example, Green and Wuts, "*Protecting Groups in Organic Synthesis*". John Wiley and Sons, 1991. The functional groups of a peptide can also be derivatized (e.g., alkylated) using art-known methods.

Peptides can be synthesized and assembled into libraries comprising a few to many discrete molecular species. Such libraries can be prepared using well-known methods of combinatorial chemistry, and can be screened as described herein or using other suitable methods to determine if the library comprises peptides which can antagonize chemokine function. Such peptide antagonists can then be isolated by suitable methods.

The term "peptidomimetic" as used herein, refers to molecules which are not polypeptides, but which mimic aspects of their structures. For example, polysaccharides can be prepared that have the same functional groups as peptides which can antagonize a chemokine. Peptidomimetics can be designed, for example, by establishing the three dimensional structure of a peptide agent in the environment in which it is bound or will bind to a chemokine. The peptidomimetic comprises at least two components, the binding moiety or moieties and the backbone or supporting structure.

The binding moieties are the chemical atoms or groups which will react or form a complex (e.g., through hydrophobic or ionic interactions) with a chemokine, for example, with the amino acid(s) at or near the ligand binding site. For example, the binding moieties in a peptidomimetic can be the same as those in a peptide antagonist of a chemokine. The binding moieties can be an atom or chemical group which reacts with the receptor in the same or similar manner as the binding moiety in a peptide antagonist of chemokine. Examples of binding moieties suitable for use in designing a peptidoinimetic; for a basic amino acid in a peptide are nitrogen containing groups, such as amines, ammoniums, guanidines and amides; or phosphoniums. Examples of binding moieties suitable for use in designing a peptidomimetic for an acidic amino acid can be, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, thereby forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more —CONH— groups for a —NHCO— group). In yet another embodiment, the peptide backbone can be substituted with a polysilane backbone.

These compounds can be manufactured by known methods. For example, a polyester peptidomimetic can be prepared by substituting a hydroxyl group for the corresponding cc-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened as described herein to determine if the library comprises one or more peptidomimetics which antagonize chemokine receptor function. Such peptidomimetic antagonists can then be isolated by suitable methods.

In one embodiment, the chemokine receptor antagonist is an antibody or antigen-binding fragment thereof having specificity to a chemokine receptor. The antibody can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, humanized, primatized, veneered or single chain antibodies. Functional fragments include antigen-binding fragments which bind to the chemokine receptor. For example, antibody fragments capable of binding to CCR I or portions thereof, including, but not limited to Fv, Fab, Fab' and F(ab)2 fragments are encompassed by the invention. Such fragments can be produced by enzymatic cleavage or by recombinant techniques. For example, papain or pepsin cleavage can generate Fab or F(ab')2 fragments, respectively. Other proteases with the requisite substrate specificity can also be used to generate Fab or $F(ab')_2$ fragments. Antibodies can also be produced in a variety of truncated forms using antibody genes in which one or more stop codons has been introduced upstream of the natural stop site. For example, a chimeric gene encoding a $F(ab')_2$ heavy chain portion can be designed to include DNA sequences encoding the $CH_1$ domain and hinge region of the heavy chain. Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0 125 023 B1; Boss et al., U.S. Pat. No. 4,816,397; Boss et al., European Patent No. 0 120 694 B1; Neuberger, M. S. et al., WO 86/01533; Neuberger, et al., European Patent No. 0 194 276 B1; Winter, U.S. Pat. No. 5,225,539; Winter, European Patent No. 0 239 400 B1; Queen et al., European Patent No. 0 451 216 B1; and Padlan, et al., EP 0 519 596 A1. See also, Newman, et al., *BioTechnology,* 10. 1455-1460 (1992), regarding primatized antibody, and Ladner et al., U.S. Pat. No. 4,946,778 and Bird, et al., *Science,* 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, et al., *Nucl. Acids Res.,* 17: 5404 (1989)); Sato, et al., *Cancer Research,* 53: 851-856 (1993); Daugherty, et al., *Nucleic Acids Res.,* 19(9): 2471-2476 (1991); and Lewis, et al., *Gene,* 101: 297-305 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for mammalian (e.g., human) chemokine receptors can be raised against an appropriate immunogen, such as isolated and/or recombinant human chemokine receptors or portions thereof (including synthetic molecules, such as synthetic peptides). Antibodies can also be raised by immunizing a suitable host (e.g., mouse) with cells that express chemokine receptors, such as activated T cells (see e.g., U.S. Pat. No. 5,440,020, the entire teachings of which are incorporated herein by reference). In addition, cells expressing recombinant chemokine receptors such as transfected cells, can be used as immunogens or in a screen for antibody which binds receptor (See e.g., Chuntharapai et al., *J. Immunol.,* 152: 1783-1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler, et al., *Nature,* 256:495-497 (1975) and *Eur. J. Immunol.* 6: 511-519 (1976); Milstein, et al., *Nature* 266: 550-552 (1977); Koprowski, et al., U.S. Pat. No. 4,172,124; Harlow, et al. 1988, Antibodies: A Laboratory Manual, (Cold Spring Harbor Laboratory: Cold Spring Harbor, N.Y.); Current Protocols In Molecular Biology, Vol. 2 (Supplement 27, Summer'94), Ausubel, et al., Eds., John Wiley & Sons: New York, N.Y.), Chapter 11, (1991)). Generally, a hybridoma is produced by fusing a suitable immortal cell line (e.g., a myeloma cell line such as SP2/0 or P3X63Ag8.653) with antibody producing cells. The antibody producing cells, preferably those obtained from the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can be used, including, for example, methods which select recombinant antibody from a library (e.g., a phage display library), or which rely upon immunization of transgenic, animals (e.g., mice) capable of producing a repertoire of human antibodies (see e.g., Jakobovits, et al., *Proc. Natl. Acad Sci.* USA, 90: 2551-2555 (1993); Jakobovits, et al., *Nature,* 362: 255-258 (1993); Lonberg, et al., U.S. Pat. No. 5,545,806; Surani, et al, U.S. Pat. No. 5,545,807; Lonberg, et al., WO 97/13852).

In one embodiment, the antibody or antigen-binding fragment thereof has specificity for a mammalian CC chemokine receptor-1, such as human CCR1. In a preferred embodiment, the antibody or antigen-binding fragment can inhibit binding of a ligand (i.e., one or more ligands) to CCR1 and/or one or more functions mediated by CCR1 in respond to ligand binding.

An "effective amount" of a chemokine antagonist is an amount sufficient to achieve a desired therapeutic and/or prophylactic effect, such as an amount sufficient to inhibit graft rejection, and/or ischemia/reperfusion injury. For example, an effective amount is an amount sufficient to inhibit a (i.e., one or more) function of a chemokine (e.g., chemokine receptor ligand-induced leukocyte migration, chemokine receptor ligand-induced integrin activation, chemokine receptor ligand-induced transient increase in the concentration of intracellular free calcium [Ca+2] and/or chemokine receptor ligand-induced secretion (e.g. degranulation) of proinflammatory mediators), and thereby, inhibit graft rejection and/or ischemia/reperfusion injury. An "effective amount" of an additional therapeutic agent (e.g., immunosuppressive agent) is an amount sufficient to achieve a desired therapeutic and/or prophylactic effect (e.g., immunosuppression).

The amount of agent (e.g., chemokine antagonist, adhesion molecule antagonist, additional therapeutic agent), administered to the individual will depend on the characteristics of the individual, such as general health, age, sex, body weight tolerance to drugs as well as the degree, severity and type of rejection and/or ischemia/reperfusion injury. The skilled artisan will be able to determine appropriate dosages depending on these and other factors. Typically, an effective amount can be from about 0.1 mg per day to about 100 mg per day for an adult. Preferably, the dosage ranges from about 1 mg per day to about 100 mg per day.

The agent (e.g., chemokine antagonist, adhesion molecule antagonist, additional therapeutic agent) can be administered by any suitable route, including, for example, orally in capsules, suspensions or tablets or by parenteral administration can include, for example, intramuscular, intravenous subcutaneous, or intraperitoneal administration. The agent (e.g., chemokine antagonist, adhesion molecule antagonist, additional therapeutic agent) can also be administered orally (e.g., dietary), transdermally, topically, by inhalation (e.g., intrabronchial, intranasal, oral inhalation or intranasal drops) or rectally. Administration can be local or systemic as indicated. The preferred mode of administration can vary depending upon the particular agent (e.g., chemokine antagonist, adhesion molecule antagonist, additional therapeutic agent) chosen, however, oral or parenteral administration is generally preferred.

The agent (e.g., chemokine antagonist, adhesion molecule antagonist, additional therapeutic agent) can be administered as a neutral compound or as a salt. Salts of compounds containing an amine or other basic group can be obtained, for example, by reacting with a suitable organic or inorganic acid, such as hydrogen chloride, hydrogen bromide, acetic, acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The antagonist of chemokine function can be administered to the individual as part of a pharmaceutical composition for inhibition of graft rejection and/or ischemia/reperfusion injury comprising a chemokine antagonist and a pharmaceutically acceptable carrier. Pharmaceutical compositions for co-therapy can comprise an antagonist of chemokine function and one or more additional therapeutic agents. An antagonist of chemokine function and an additional therapeutic agent can be components of separate pharmaceutical compositions which can be mixed together prior to administration or administered separately. Formulation will vary according to the route of administration selected (e.g., solution, emulsion, capsule). Suitable pharmaceutical carriers can contain inert ingredients which do not interact with the antagonist of chemokine function and/or additional therapeutic agent. Standard pharmaceutical formulation techniques can be employed, such as those described in Remington's Pharmaceutical Sciences, Mack Publishing Company, Easton, Pa.

Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringers-lactate and the like. Methods for encapsulating compositions (such as in a coating of hard gelatin or cyclodextran) are known in the art (Baker, et al., "Controlled Release of Biological Active Agents", John Wiley and Sons, 1986).

The present invention will now be illustrated by the following Examples, which are not intended to be limiting in any way.

Allogeneic Methods

The methods described herein are used where, as between the donor and recipient, there is any degree of mismatch at MHC loci or other loci which influence graft rejection. Unlike conventional bone marrow transplantation, mismatch is desirable in methods of the invention, as mismatch promotes GVL effects. Methods of the invention are used where, as between allogeneic donor and recipient, there is a mismatch at least one MHC locus or at least one other locus that mediates recognition and rejection, e.g., a minor antigen locus. With respect to class I and class II MHC loci, the donor and recipient are: matched at class I and mismatched at class II; mismatched at class I and matched at class II; mismatched at class I and mismatched at class II; matched at class I, matched at class II. Mismatched, at class I or II, means mismatched at one or two haplotypes. Mismatched at MHC class I means mismatched for one or more MHC class I loci, e.g., in the case of humans, mismatched at one or more of HLA-A, HLA-B, or HLA-C. Mismatched at MHC class II means mismatched at one or more MHC class II loci, e.g., in the case of humans, mismatched at one or more of a DP α, a DPβ, a DQ α, a DQ β, a DR α, or a DR β. In any of these combinations other loci which control recognition and rejection, e.g., minor antigen loci, are matched or mismatched. It is preferable that there is mismatch at least one class I or class II locus and, more preferably, mismatch at one class I and one class II locus.

The methods described herein for inducing tolerance to an allogeneic antigen or allogeneic graft are used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests are used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

In preferred embodiments the donor and the subject are not related, e.g., the donor is not a sibling, the offspring of, or the parent of the recipient.

Xenogeneic Methods

Methods of the invention use xenogeneic donors, e.g., when the subject is a human, the donor is a non-human primate or a swine, preferably a miniature swine.

Hematopoietic Stem Cells

Methods of the invention require the introduction of donor hematopoietic stem cells. Administration and engraftment of the donor stem cells converts the subject to a mixed chimera. Because donor hematopoietic stem cells are at a competitive disadvantage to subject hematopoietic stem cells, it is often desirable to create hematopoietic space in the donor, in order to promote engraftment of the donor cells. Methods of the invention use mild non-myeloablative methods, e.g., the administration of cyclophosphamide, to create hematopoietic space. However, if a sufficient number of donor cells are administered, the subject need not receive space-creating treatment. See e.g., U.S. patent application Ser. No. 08/855,705, filed Is 8, 1997, hereby incorporated by reference. Thus, other methods of the invention administer a sufficient number of donor hematopoietic stem cells such that the creation of space, even with mild methods, is not required. This approach is particularly useful in xenogeneic methods, especially those in which very large numbers of donor hematopoietic stem cells are available, e.g., when the donor or donors are inbred miniature swine.

The number of donor stem cells administered to the recipient is increased by either increasing the number of stem cells provided in a particular administration or by providing repeated administrations of donor stem cells.

Repeated stem cell administration promotes engraftment and mixed chimerism in recipients. In preferred embodiments, particularly xenogeneic embodiments, multiple administrations of donor stem cells are provided. A second (or other subsequent) administration of hematopoietic stem cell is provided: at least two days, one week, one month, or six months after the previous administration of stem cells; when tumor regression is below desired levels; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells; or generally, as is needed to maintain tumor regression.

When multiple stem cell administrations are given one or more of the administrations include a number of donor hematopoietic cells which is at least twice, is equal to, or is at least 75, 50, or 25% as great as, the number of bone marrow cells found in an adult of the recipient species; include a number of donor hematopoietic stem cells which is at least twice, is equal to, or is at least 75, 50, or 25% as great as, the number of bone marrow hematopoietic stem cells found in an adult of the recipient species. Such large numbers are useful in reducing or eliminating the need for space creating treatment, even mild treatments.

The method of introducing stem cells is altered, particularly by (1) increasing the time interval between administering injecting hematopoietic stem cells and space creating treatment or leukocyte infusion; (2) increasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension is used; or (6) varying the donor source of hematopoietic stem cells. Although hematopoietic stem cells derived from the leukocyte donor are preferable, hematopoietic stem cells are obtained from other individuals or species, or from genetically-engineered inbred donor strains, or from in vitro cell culture.

Sources of Cells for Allogeneic Stem Cell Transplantation

A living human donor provides about $7.5 \times 10^8$ bone marrow cells/kg. Methods of the invention include the administration of at least 2 or 3 times this number (per kg) especially when it is desired to reduce or eliminate space creating treatments, and preferably at least 10, 15, or 20 times this number. Such large numbers are useful in reducing or eliminating the need for space creating treatment, even mild treatments. The requisite numbers of bone marrow cells are provided by the ex vivo expansion or amplification of human stem cells. Ex vivo expansion is reviewed in Emerson, 1996, *Blood* 87:3082, hereby incorporated by reference. Methods of ex vivo expansion are described in more detail in Petzer, et al., 1996, *Proc. Natl. Acad. Sci. USA* 93:1470; Zundstra, et al., 1994, *Bio-Technology* 12:909; and Davis, et al., WO 95 11692, all of which are hereby incorporated by reference. Sources of hematopoietic stem cells include bone marrow cells, mobilized peripheral blood cells, and when available cord blood cells.

Sources of Cells for Xenogeneic Stem Cell Transplantation

In the case of inbred donor animals, e.g., inbred miniature swine, very large numbers of stem cells are available, as the number which are supplied is not limited by the number which are harvested from a single donor.

In the case where the recipient is a primate, e.g., a human, and the donor is a swine, e.g., a miniature swine, $7.5 \times 10^9$ or more, and preferably, between $7.5 \times 10^9$ and $15 \times 10^{10}$, swine bone marrow cells/kg are administered, though this will vary with factors such as the intensity of the preparative regimen and the health of the individual recipient. Such large numbers are useful in reducing or eliminating the need for space creating treatment, even mild treatments. As discussed herein, these cells are provided in more than one administration.

The invention is further illustrated by the following examples that should not be construed as limiting. The contents of all references, patents and published patent applications cited throughout this application are incorporated herein by reference.

EXAMPLES

Treatment of Hematologic Cancers

The following provides a protocol for the treatment of a human subject having a hematologic cancer in a preliminary clinical setting. The protocol describes the major components of the treatment, the therapy to be provided to the subject, pre- and post-treatment evaluation, and supportive care likely to be needed in the course of the treatment. This protocol is exemplary of an embodiment of the invention and is not limiting.

The treatment consists of four major components:
1. Conditioning therapy, e.g., with cyclophosphamide 200 mg/kg and thymic irradiation (7 Gy) and BMT.
2. GVHD prophylaxis, e.g., with anti-thymocyte globulin (ATG) and cyclosporine.
3. Post-transplant supportive care (antibiotics, transfusional support, hemopoietic growth factors, etc.)
4. Donor leukocyte infusions (days +35, +56).
5. Thymic irradiation except subjects who have received previous mediastinal radiation therapy. Scheme of therapy is as follows:

Day Treatment
−6 Cyclophosphamide 50 mg/kg
−5 Cyclophosphamide 50 mg/kg
−4 Cyclophosphamide 50 mg/kg
−3 Cyclophosphamide 50 mg/kg
−2 ATG 15 mg/kg
−1 Thymic irradiation (7 Gy), ATG 15 mg/kg, CYA 5 mg/kg IV
0 Bone marrow infusion, CYA 5 mg/kg IV
+1 ATG 15 mg/kg
+4 CYA 3 mg/kg IV
+15 CYA 12 mg/kg PO
+30 CYA 12 mg/kg PO +35-49 Donor leukocyte infusion Treatment modalities referred to in the scheme of therapy are as follows:

A. Cyclophosphamide (Cytoxan™)
1. Dosage: cyclophosphamide is administered at a dosage of 50 mg/kg on days −6, −5, −4, and −3. cyclophosphamide is dissolved in distilled water and administered over 60 minutes. Dose should be calculated based on actual or ideal body weight, whichever is less. Volume of distilled water to be used is 250 ml for adults.
2. Sedation, antinausea: Dexamethasone, Diphenhydramine, Lorazepan and Granisetron prior to cyclophosphamide.
3. Because of a 20% incidence of hemorrhagic cystitis, the following plan of fluid administration and management is recommended for prevention:
    a. IV hydration fluids for adults should be at 3000 ml/m$^2$/24 hours, beginning 4 hours prior to cyclophosphamide administration. Typically the hydration fluid is $D_5NS+$ 20 mEq KCL/liter. This fluid should be continued for 24 hours after the last dose of cyclophosphamide.
    b. MESNA at a dose of 15 mg/kg will be administered 15 minutes before and 3, 6, and 9 hours after cyclophosphamide (with an additional dose 24 hours after the fourth IV dose).
    c. Additional KCL and $NaHCO_2$ is be needed depending on subject's electrolyte and uric acid status.
4. Toxicity and complications
    a. Nausea and vomiting. Variable but usually well controlled with anti emetics.
    b. Uric acid nephropathy. A potential problem that is easily prevented by high urine flow plus alkalinization and allopurinol.
    c. Fluid retention. cyclophosphamide causes an antidiuretic effect usually counteracted by furosemide administration. Careful physical examination and accurate weights three times a day should be able to detect fluid overload early.
    d. Cardiomyopathy. cyclophosphamide causes nonspecific ST changes at this dose level and at total doses ≧200 mg/kg (7.6 grams/m$^2$) fatal cardiac failure due to hemorrhagic necrosis occurs. cyclophosphamide is contraindicated in subjects with pre-existing cardiac disease. Subjects should receive an EKG on admission, on each day cyclophosphamide is given, and 1 day following cyclophosphamide.
    e. Diarrhea. Is be a problem and should be treated symptomatically with Tincture of Opium (dose is 1-3 drops/dose) or Immodium. Stool volume loss should be replaced with $D_5W$ and an appropriate electrolyte solution.
    f. Hemorrhagic cystitis. Approximately 50% of subjects will have some hernaturia at this dose level, but is usually not symptomatic or severe unless there is inadequate diuresis. An occasional subject will get severe cystitis despite adequate urine flow.
    g. Alopecia. The subject should be told of hair loss prior to drug administration.
    h. Skin rash. 10-20% of subjects develop a diffuse maculopapular rash 24-72 hours following cyclophosphamide. The rash usually resolves in 24-48 hours.
    i. Anemia. Hematocrit decrements out of proportion to cessation of production will occur at this dose, presumably due to hemolysis.
    j. Electrolyte imbalance. This should be anticipated and daily electrolytes followed.

B. Anti-thymocyte Globulin (ATG; ATGAM™, Upjohn Co.)
1. Dosage: ATG is prepared in 1 liter of normal saline and is given at a dose of 15 mg/kg over 10-12 hours on days −2, −1, and +1. The dose of ATG will be based on ideal or actual body weight, whichever is less.
2. Skin Testing
    a. All subjects will receive an intradermal skin test (0.1 ml of a 1 mg/ml solution) and observed for 30 minutes for the presence of a wheat/flare reaction. If positive, an alternative treatment plan is to be considered by the principal investigator. Benadryl 50 mg IV, epinephrine (1:1000 solution) and hydrocortisone 100 mg IV will be available at the bedside in the event of a possible allergic reaction.
3. Pre-Medication
    a. All subjects will receive dexamethasone 10 mg IV Q 12 hrs on days −2, −1, and +1. Each ATG infusion will be preceded by Benadryl IV and Tylenol 650 mg.
4. Toxicities
    a. Allergic reactions (including anaphylaxis), rash, fevers, rigors, arthralgias, myalgias, dyspnea, serum sickness (including rash, arthritis, proteinuria), hypotension, tachycardia.

C. Cyclosporine (Sandimmune™, Sandoz Co.)
1. Cyclosporine is commercially available and is administered either in an intravenous form (mixed in 250 ml of distilled water), or an oral olive oil based solution, or in capsule form (100 and 25 mg capsules).
2. All subjects will receive cyclosporine starting on day −1 at a dose of 5 mg/kg/day intravenously infused over a period of 20 hours daily. The dose will be reduced to 3 mg/kg/day on day +4 until the subject is able to tolerate p.o. cyclosporine (on or after day +15 post-transplant) at a dose of 6 mg/kg twice daily. Cyclosporine will be dose adjusted on the following criteria:
    a. Cyclosporine levels: an attempt will be made to keep cyclosporine dose levels within the therapeutic range (between 250-350 mg/ml by monoclonal assay). Given an association between low cyclosporine levels and the development of acute GVHD, attempts will be made to keep the level in the high normal range particularly during the first 4 weeks post transplant.
    b. Dose reduction should be considered for significant renal dysfunction (e.g. greater than a 50% increase from baseline serum creatinine level particularly accompanied by a high cyclosporine level).
    c. Careful attention should be given to cyclosporine levels and renal function in the face of hepatic disease, given the extent of hepatic metabolism of cyclosporine.
    d. In the absence of acute GVHD, cyclosporine will be tapered and discontinued by day +30 post-transplant.

D. Thymic Irradiation
1. 7 Gy of thymic irradiation will be administered in a single dose on day −1.
2. Possible toxicities of thymic irradiation include bone marrow suppression, nausea, vomiting, esophagitis, pneumonitis, pericarditis and secondary malignancy.

E. Bone Marrow Infusion
1. Allogeneic bone marrow will be rapidly infused intravenously without a filter as soon as possible after harvest.
    a. Acute toxicities:
        1. Pulmonary emboli. Marrow and fat emboli rarely causes a transient alveolar capillary block and temporary administration Of $O_2$ is necessary.

2. Hypotension.
3. Volume overload.

F. Donor Leukocyte Infusion(s)
1. Donor peripheral blood mononuclear cells will be collected via leukophoresis on days +35 and +56 post-transplant. Based on established anti-tumor efficacy of $1\times10^7$/kg T-cells in CML and reduced risk of GVHD with this dose compared with $\geq 5\times10^7$/kg T-cells (34), an initial infusion (day +35) of $1\times10^7$/kg CD3+T-cells will be performed. If no GVHD is observed and full donor (greater than or equal to 90%) chimerism has not been established, or if there is evidence of persistent malignancy, a second dose of $10^7$/kg T-cells will be infused on day +56 post-transplant.
2. Recipient risks of receiving donor leukocyte infusions include acute and chronic GVHD and marrow aplasia.

Evaluation

The following protocol is be used to evaluate prospective recipients.

A. Pre-transplant
1. History. A complete history with full details of the subject's previous treatment and response will be obtained, including:
    a. Subject exposure to steroids, radiation and antileukemic drugs (total dosage of each antileukemic drug and when given).
    b. Previous or current fever, infections and antibiotic treatment.
    c. Previous CNS involvement and other evidence of extramedullary leukemia.
    d. Clinical picture at initial presentation including Karnofsky score.
    e. Prior immunologic and cytogenetic studies of the subject's leukemic cells.
2. Clinical evaluation (all measurements in metric units).
    a. A complete physical examination.
    b. Chest and other radiographs as clinically indicated.
    c. Marrow aspiration and biopsy for staging and cytogenetics.
    d. EKG
    e. Dental consult and evaluation of status of teeth and gums.
    f. Lumbar puncture(s) for determination of presence of CNS leukemia and administration of IT therapy for subjects with intermediate to high grade non-Hodgkin's lymphoma.
    g. Pulmonary consult for baseline respiratory studies, with room air arterial blood gas.
3. The following laboratory data should be obtained:
    a. ABO and Rh typing and two-way red cell crossmatch with donor.
    b. HLA typing of subject and available family members and potential platelet donors.
    c. Hepatitis B surface antigen, HCV, HSV, CMV, HIV and HTLV-1 antibody determinations for subject and marrow donors.
    d. Cultures of blood, stool, urine, nose, and throat for potential pathogenic bacteria, viruses and fungi.
    e. CBC, reticulocyte count, chem 20 and toxoplasma titers. 10 ml serum (2 dry red tops) and 20 cc of heparinized blood (2 green tops) for immunologic studies.
    f. Lymphoma or leukemia cells, from marrow or peripheral blood, if available, to be frozen in DMSO for later immunologic studies.

The following protocol is to be used to monitor subjects who receive treatment with methods of the invention.

B. Evaluation During Conditioning and the First 100 Days Post-transplantation
1. Daily CBC until granulocytes and platelets are self-sustaining; at least three times weekly until discharge, and then once or twice weekly until 100 days post-transplant.
2. Daily chemistry profile for the first 3 weeks, then as clinically indicated, but at least once weekly.
3. Marrow aspiration and biopsy on day 28 and 100 post-transplant.
4. Chest x-ray every 7 days.
5. Serum to serum bank (10 ml clotted blood) every 7 days.
6. Viral, bacterial and fungal cultures weekly or when clinically indicated or as specified in other protocols until discharge, then as clinically indicated.
7. EKG daily during and 1 day after last dose of cyclophosphamide.
8. Daily weights.
9. Respiratory function tests per attending.
10. Blood for CSP levels every Monday or as per attending.
11. Screening studies for chronic GVHD on day 100.
12. Chimerism studies: see study parameter (section XI).

C. Evaluation Following 100 Days Post-transplant
1. Monthly evaluations here for local subjects and by referring physicians for subjects who live elsewhere for one year following engraftment.
2. Monthly CBC and chem 20 for 6 months. Marrow aspiration as indicated clinically or required by other protocols.
3. Periodic studies as per other specific protocols.
4. Complete evaluation every 6 months for 2 years, then annually.

Supportive Care

The following outlines supportive care which is appropriate.

A. Access to vessels. All subjects will have placement of a silastic indwelling triple lumen central venous catheter (or have dual double lumen catheters) on or before admission.
B. Hyperalimentation (HAL). Some subjects will require hyperalimentation soon after conditioning. Given the hepatotoxic potential of HAL, caloric intake will be adjusted to provide approximately 50 to 75% of the calculated need.
C. Transfusions.
1. Indication. Platelets are transfused to prevent bleeding and an attempt will be made to keep the circulating platelet level $>20\times10^9$/L at all times. Packed red blood cells will be transfused to maintain a hematocrit of $\geq 25\%$.
2. Single donor apheresis platelet products containing a minimum equivalent of 6 units of random donor platelets will be preferentially used.
3. Subjects will have their CMV serostatus determined prior to conditioning therapy. CMV negative subjects will receive CMV negative blood products as available.
4. All platelet and red cell transfusions will be white blood depleted using third generation leukocyte filters.
5. Irradiation. All products are irradiated with 2500 rad (from a 137/Cs irradiator) prior to infusion to inactivate lymphocytes and prevent a transfusion associated GVHD.
6. Problems.
    a. Alloimmunization. Subjects frequently become refractory to mismatched platelets due to alloimmunization to HLA and platelet antigens. For practical purposes, this is established by failure to demonstrate an adequate increment 60 minutes after a 4-6 unit equivalent transfusion. If non-family platelets are required and the subject is immunized to random donors, attempts should be made to locate an unrelated platelet donor with no HLA antigens in excess of the recipient. Mismatched platelets is harmful in the presence of alloimmunization, with chills, fever and a drop in circulating platelet and neutrophil levels.

b. Consumption. These subjects have complicated problems leading to rapid consumption of platelets, and the distinction between this and alloimmunization is often difficult. Subjects who demonstrate an adequate post-transfusion increment but have rapid disappearance of platelets are assumed to have consumption and will be given more frequent platelet transfusions.

c. Allergic reactions. Chills, fever, and hives occasionally occur despite adequate circulation of platelets. These are presumed to be allergic reactions to antigens other than HLA or platelet antigens and is controlled with diphenhydramine. However, if associated with no increment or with a decrement, these reactions are probably associated with alloimmunization to the transfused platelets and that donor should not be used again.

D. Management of infections. Principals of infection prophylaxis and treatment will vary according to the spectrum of organisms and their antibiotic sensitivity and concurrent infection management/antibiotic clinical trials. General principals of infection management will include:
1. reduced bacteria diet
2. HEPA filtered or LAF protective isolation
3. Oral Ofloxacin 400 mg BID, from admission until ANC is >0.5×10$^9$/L for antibacterial prophylaxis.
4. Acyclovir 250 mg/m$^2$ IV or PO q8h days −1 until discharge for HSV prophylaxis.
5. Fluconazole PO or IV days −1 until ANC is >0.5×10$^9$/L for antifungal prophylaxis.
6. Broad spectrum antibiotics for fever (T≧100$^5$) in the face of neutropenia with continuation of antibiotics until ANC is >0.5×10$^9$/L. Antibiotic choice will vary but will usually consist of vancomycin and a third generation cephalosporin (e.g. ceftazidime) or imipenem. Aminoglycosides should be avoided if possible in view of potential synergistic renal toxicity with CSP and IL2.
7. For CMV prophylaxis/therapy:
   a. CMV negative blood products for CMV seronegative recipients.
   b. IVIG 500 mg/kg/week days −8 through +28, then every other week through day +100.
   c. DHPG for positive CMV culture or positive antigen assay.

These procedures are employed in combination, as described, or in part These procedures are designed to synergistically prevent the problem of GVHD while maximizing the GVL effect of donor tissue.

Mixed Lymphohematopoietic Chimerism Following a Non-myeloablative Conditioning Regimen and Allogeneic Bone Marrow Transplant (BMT)

Five subjects with chemotherapy (n=5) and radiation (n=2) refractory non-Hodgkin's lymphoma were treated with cyclophosphamide (Cy) 50 mg/kg daily×4 (days −6 through −3), anti-thymocyte globulin 30 mg/kg (days −2, −1, +1) thymic irradiation 700 cGy×1 (n=3) (day −1) and HLA genotypically identical (n=2), phenotypically identical (n=1), or 2 antigen mismatched donor BMT (day 0). Intravenous cyclosporine (CYA) was given beginning on day −1 with conversion to p.o. CYA when tolerated. Donor leukocytes (DLI) were given on days +35, (10$^7$/kg CD3+ cells) and +56 (5×10$^7$/kg CD3+ cells) if no GVHD was present. Median subject age was 30 (range 20-45) years. All subjects had disease progression during salvage chemotherapy or radiation therapy. Toxicities have included reversible Cy cardiotoxicity (n=1), and capillary leak syndrome coincident with engraftment (n=4). Median times to ANC>0.5 and platelets>20 K have been 16 (range 13-17) and 16 (range 8 to 91+) days. Chimerism analyses of weekly peripheral blood samples and pre-BMT, day +28, and day +100 bone marrow aspirate samples have been performed by variable number of tandem repeat sequence (VNTR) analysis (HLA matched BMT) or flow cytometry (HLA mismatched BMT). In recipients of HLA-matched marrow (n=3) mixed chimerism was seen in all three. One subject had conversion to full donor chimerism following DLI and developed grade III GI GVHD. One subject had ≦10% donor cells; at day +35 he had no detectable donor cells. No donor cells were detectable after a subsequent DLI. The third subject has 50-70% donor cells on day +28 with grade II cutaneous GVHD. In the two recipients of HLA-2 antigen mismatched marrow, >90% donor lymphoid chimerism was seen within 2 weeks of BMT coincident with grade II or III GVHD. In one subject gradual conversion to donor myeloid (neutrophils and monocytes) chimerism was observed. In the other subject stable "split" lymphohematopoietic chimerism is present (>90% donor lymphoid, >80% host myeloid). All subjects are alive at a median of 103 days (range 3y-122 days) following BMT. Four of five subjects are clinically disease-free at the present time. Mixed lymphohematopoietic chimerism is achievable following a novel non-myeloablative conditioning regimen and HLA-matched or mismatched BMT. Dramatic anti-tumor responses have been seen in the majority of cases.

Activation-induced Cell Death in Donor TCR Transgenic T Cells with Known Host Antigen Specificity The expansion and elimination of donor T cell receptor (TCR) transgenic T cells with known host antigen specificity was examined in a murine BMT model. In 2C T-cell receptor transgenic mice (H-2$^b$ on B6 background), a large fraction of T cells express CD8 and the αβ T-cell receptor from the cytotoxic T lymphocyte clone 2C, which specifically recognizes the MHC class I antigen L$^d$ (Sha, W. C. et al., Nature 335, 271-274 1988). Lethally irradiated, L$^{d+}$ BALB/c (H-2$^d$) mice were transplanted with 10×10$^6$ spleen cells from anti-L$^d$ 2C TCR-transgenic B6 mice. By 4 days after BMT, the numbers of 2C CD8 cells in the spleens of BALB/c recipients had increased 14-16 fold over the number administered. However, they had drastically decreased to similar numbers to those administered by day 7. By 3-color FCM using 7-AAD (amino-actinomycin-D) for DNA staining, we found that an increasing fraction (4-11%) of GVH-reactive 2C CD8 cells in spleens of 2C→BALB/c recipients underwent apoptotic cell death between days 4 and 7 after BMT, coincident with the observed decrease in absolute numbers of 2C CD8 cells in recipients' spleens. In addition, 2C CD8 cells showed reduced expression of 2C TCR and CD8 on days 4, 7, and 21. They also demonstrated anergy upon stimulation with anti-αβTCR and 1B2 (anti-2C clonotypic mAb) mAbs at these time points. 2C CD8 cells remaining on day +21 expressed the CD45RB$^{low}$ CD44$^{high}$ Mel14$^{low}$, previously activated/memory phenotype. Clinically, the recipients did not show any evidence of acute GVHD, and all animals survived beyond day 80, although some of them exhibited mild chronic GVHD. The early clonal expansion of 2C CD8 cells, down-regulation of CD8 and TCR, anergy and deletion of 2C CD8 cells via activation-induced cell death, are all the consequences of a vigorous immune response. However, this marked monoclonal expansion of GVH-reactive 2C CD8 cells is incapable of inducing severe acute or subacute GVHD.

Levels of Chemokines Following Lethal Irradiation in Mice

Date BMT (=d0)
Goal: 1. Induce GVHD to harvest tissues
2. Study effect of conditioning toxicity Groups A&B
BM Donors: BALB/c, B6
Recipient: B6

Conditioning Regimen: Group A&B 975 rad TBI

| Groups | Recipient | B6BMC $1 \times 10^7$ | BALB/c BMC $1 \times 10^7$ +13 $\times 10^7$ SPC |
|---|---|---|---|
| A n = 12 | B6 | + | − |
| B n = 12 | B6 | − | + |

Figure 1:
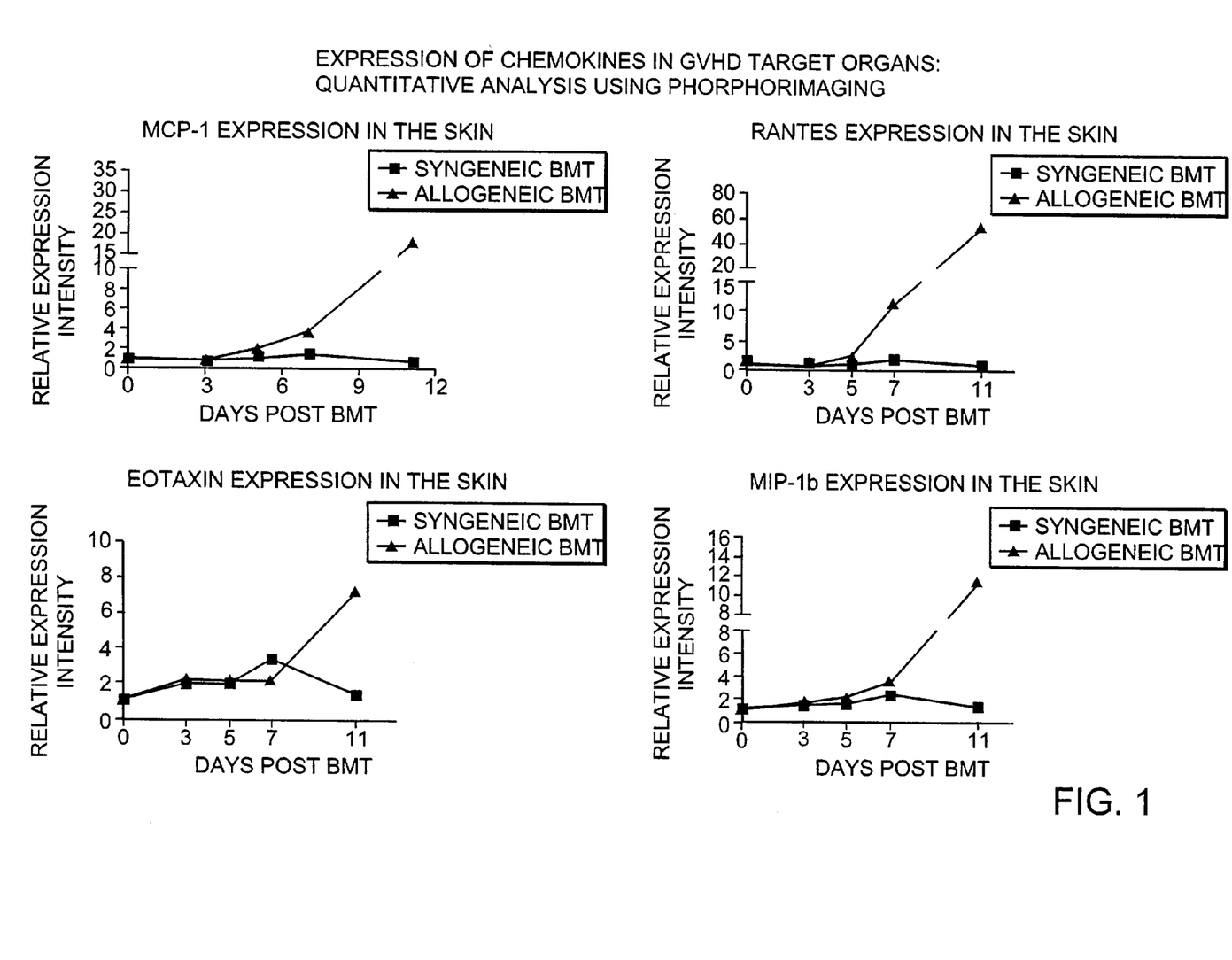
FIG. 1 is a graphic representation of the upregulation of chemokines following lethal irradiation in both syngeneic and allogeneic BMT recipients in skin tissue.
Figure 2:
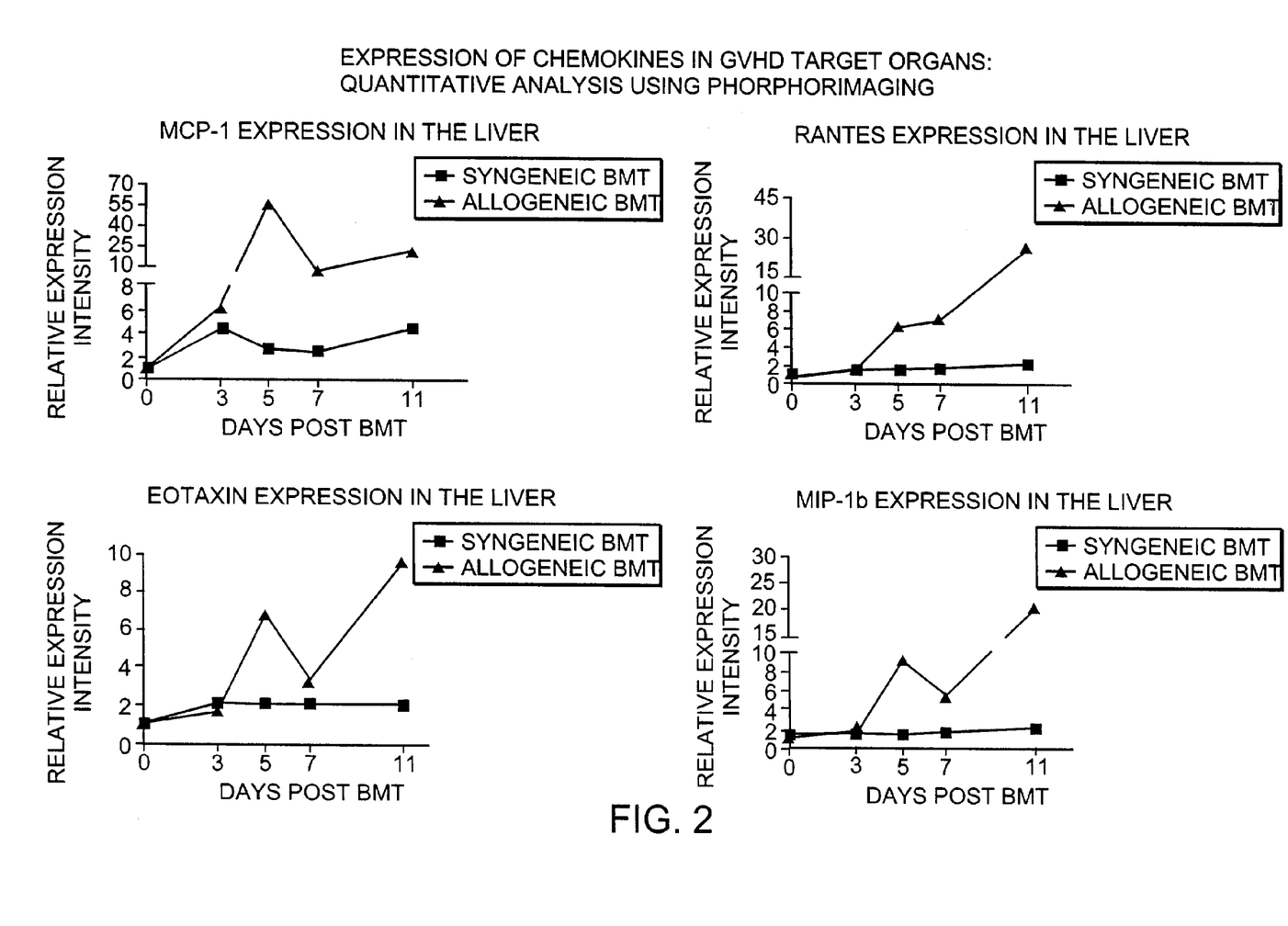
FIG. 2 is a graphic representation of the upregulation of chemokines following lethal irradiation in both syngeneic and allogeneic BMT recipients in liver tissue.
Figure 3:
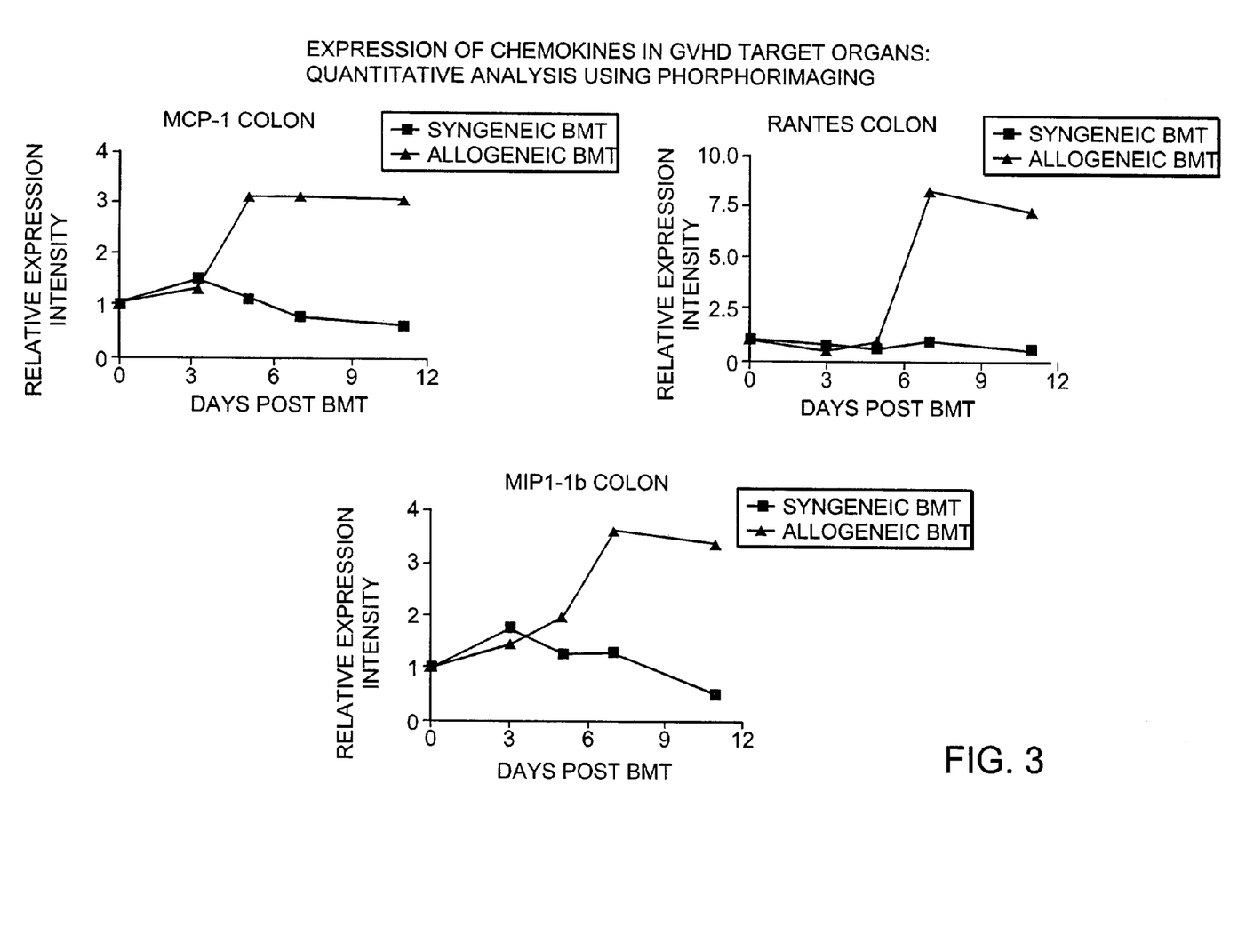
FIG. 3 is a graphic representation of the upregulation of chemokines following lethal irradiation in both syngeneic and allogeneic BMT recipients in colon tissue.

Lethal Irradiation (Group A&B):
SAC 3 animals on day 3, 5, 7, 14:

The results, as shown in FIGS. 1-3, demonstrate that chemokines were upregulated early following lethal irradiation in both syngeneic and allogeneic BMT recipients. Skin showed an upregulation of eotaxin (FIG. 1); liver showed an upregulation of MCP-1 and eotaxin (FIG. 2). In all cases, the chemokine expression declined in syngeneic recipients after day 3m, but increased further in allogeneic recipients. Additional chemokines appeared later in the tissues of allogeneic recipients. These results show that early chemokine upregulation is induced by conditioning and contributes to the infiltration of alloreactive T cells into GVHD target tissues. The alloreactive T cell infiltrates then induce a further cascade of multiple chemokine upregulation.

Administration of an Antagonist of T-cell Migration

B6 recipient mice in groups A, B, and C are treated with the same conditioning regimen (950 rad). Group A receives bone marrow from B6 donor mice. Groups B and C receive bone marrow from BALB/c donor mice. $1 \times 10^7$ BMC and $13 \times 10^6$ SPC (groups B and C) are administered on day $d_0$ of the experiment. Mice in group B receive 100 ug/mouse of anti-IP-10 antibodies per day, given every day of the experiment, starting at day $d_{-1}$.

| Groups | B6 BMC $10^7$ | BALB/c BMC +BALB/c SPC + α-IP-10 | BALB/c BMC +BALB/c SPC + hamster IgG |
|---|---|---|---|
| A n = 10 | + | − | − |
| B n = 10 | − | + | − |
| C n = 10 | − | − | + |

Surival and health of the mice are studied by observation and by weighing mice and scoring GVHD twice weekly through day 20. After day 20 mice are weighed and scored for GVHD once weekly. Survival and GVHD are compared among the three groups of mice.

Other Embodiments

As an alternative or adjunct to hemoperfusion, host antibodies may be depleted by administration of an excess of hematopoietic cells.

An anti-CD2 antibody, preferably a monoclonal, e.g., BTI-322, or a monoclonal directed to a similar or overlapping epitope, is used in addition to or in place of any anti-T cell antibodies (e.g., ATG) in any method referred to herein.

Methods of preparing the recipient for transplant of hematopoietic stem cells may vary. For instance, the recipient may undergo a splenectomy. The latter would preferably be administered prior to the non-myeloablative regimen, e.g., at day −14.

What is claimed is:

1. A method of reducing GVHD in a recipient of a hematopoietic graft, the method comprising:
   (a) administering a myeloablative or myeloreductive non-myeloablative treatment to the recipient in an amount sufficient to induce mixed chimerism;
   (b) treating the recipient with an immunosuppressive regimen in an amount sufficient to prevent rejection of donor hematopoietic cells;
   (c) introducing donor hematopoietic cells into the recipient; and
   (d) administering at least one antagonist of T-cell migration to said recipient, whereby migration of T cells into tissues of said recipient and consequent GVHD is reduced.

2. The method of claim 1, wherein the recipient has a hematologic malignancy.

3. The method of claim 1, wherein the recipient has a non-neoplastic hematologic disorder.

4. The method of claim 1, wherein the donor hematopoietic cells comprise bone marrow cells.

5. The method of claim 1, wherein the donor and the recipient are HLA-matched siblings.

6. The method of claim 1, wherein the donor and the recipient are genetically non-identical at one or more MHC loci.

7. The method of claim 1, wherein the method results in full hematopoietic chimerism.

8. The method of claim 1, wherein the antagonist of T-cell migration is an antagonist of chemokine function.

9. The method of claim 8, wherein the antagonist of chemokine function is an antagonist of at least one chemokine selected from the group consisting of IP-10, Mig, MIP-1α, MIP-1β, MIP-1γ, NAP-2, eotaxin, MCP1, MCP2, MCP3, MCP4, MCP5, and RANTES.

10. The method of claim 1 wherein the immunosuppressive regimen is in an amount insufficient to prevent a graft-versus-host response.

11. The method of claim 10, wherein the immunosuppressive regimen comprises treatment with T cell-depleting antibodies.

12. The method of claim 11, wherein the T-cell depleting antibodies are anti-CD4 or anti-CD8 antibodies.

13. The method of claim 1, further comprising administering at least one cytoreductive agent to the recipient.

14. The method of claim 13, wherein the cytoreductive agent is selected from the group consisting of alkylating agents, alkyl sulphonates, nitrosoureas, triazenes, antimetabolites, pyrimidine analogs, purine analogs, vinca alkaloids, epidophyllotoxins, antibiotics, dibromomannitol, deoxyspergualin, dimethyl myleran, and thiotepa.

15. The method of claim 1, further comprising the administration of a treatment to create thymic space.

16. The method of claim 15, wherein the thymic space-creating treatment is thymic irradiation.

* * * * *